US009920274B2

(12) United States Patent
Maruyama

(10) Patent No.: US 9,920,274 B2
(45) Date of Patent: Mar. 20, 2018

(54) LUBRICANT COMPOSITION, USE THEREOF AND ALIPHATIC ETHER COMPOUND

(71) Applicant: MORESCO CORPORATION, Kobe-Shi, Hyogo (JP)

(72) Inventor: Shingo Maruyama, Kobe (JP)

(73) Assignee: MORESCO CORPORATION, Hyogo (JP)

( * ) Notice: Subject to any disclaimer, the term of this patent is extended or adjusted under 35 U.S.C. 154(b) by 0 days.

(21) Appl. No.: 15/129,757

(22) PCT Filed: Oct. 21, 2015

(86) PCT No.: PCT/JP2015/079666
§ 371 (c)(1),
(2) Date: Sep. 27, 2016

(87) PCT Pub. No.: WO2016/129148
PCT Pub. Date: Aug. 18, 2016

(65) Prior Publication Data
US 2017/0183598 A1    Jun. 29, 2017

(30) Foreign Application Priority Data

Feb. 9, 2015  (JP) ................. 2015-023672

(51) Int. Cl.
  *C10M 107/32*  (2006.01)
  *C10M 133/12*  (2006.01)
  (Continued)

(52) U.S. Cl.
  CPC ........... *C10M 133/12* (2013.01); *C07C 43/10* (2013.01); *C10M 105/18* (2013.01);
  (Continued)

(58) Field of Classification Search
  CPC .............. C10M 2207/0406; C10M 2209/1033
  (Continued)

(56) References Cited

U.S. PATENT DOCUMENTS 5,084,194 A    1/1992  Doner et al.
5,256,320 A   10/1993  Todd et al.
  (Continued)

FOREIGN PATENT DOCUMENTS

JP    S60-217298 A   10/1985
JP    S63-61038 A     3/1988
  (Continued)

OTHER PUBLICATIONS

Decision to Grant a Patent for JP Patent Application 2015-555885, dated Jan. 26, 2016 (in Japanese with full English Translation).
  (Continued)

*Primary Examiner* — Ellen M McAvoy
(74) *Attorney, Agent, or Firm* — Harness, Dickey and Pierce, P.L.C.

(57) ABSTRACT

The present invention provides a lubricant composition having high moisture resistance and having physical properties including low viscosity, low evaporability, low-temperature fluidity, and a high viscosity index. The lubricant composition contains (i) an aliphatic ether compound as a base oil and (ii) an antioxidant made from at least alkylated phenylnaphthylamine and phosphite ester, wherein a sum of individual amounts of the alkylated phenylnaphthylamine and the phosphite ester is a predetermined amount, and the alkylated phenylnaphthylamine and the phosphite ester are used in a predetermined ratio.

15 Claims, 12 Drawing Sheets

(51) Int. Cl.
  *C10M 105/18* (2006.01)
  *C10M 137/02* (2006.01)
  *C07C 43/10* (2006.01)
  *F16C 33/10* (2006.01)

(52) U.S. Cl.
  CPC ......... *C10M 137/02* (2013.01); *F16C 33/109* (2013.01); *C10M 2207/0406* (2013.01); *C10M 2215/065* (2013.01); *C10M 2223/049* (2013.01); *C10N 2230/02* (2013.01); *C10N 2230/10* (2013.01); *C10N 2240/02* (2013.01); *C10N 2250/10* (2013.01); *F16C 2370/12* (2013.01)

(58) Field of Classification Search
  USPC ......................................................... 508/579
  See application file for complete search history.

(56) References Cited

U.S. PATENT DOCUMENTS

| | | | |
|---|---|---|---|
| 5,256,321 A | 10/1993 | Todd | |
| 5,262,076 A | 11/1993 | Ishida et al. | |
| 5,354,485 A | 10/1994 | Tipton et al. | |
| 5,403,501 A | 4/1995 | Schwind | |
| 5,464,548 A | 11/1995 | Cahoon et al. | |
| 5,576,281 A * | 11/1996 | Bunch | C07C 43/11 510/220 |
| 5,596,039 A | 1/1997 | Oishi et al. | |
| 5,674,947 A | 10/1997 | Oishi et al. | |
| 6,582,621 B1 | 6/2003 | Sasaki et al. | |
| 8,334,323 B2 * | 12/2012 | Varineau | C07C 41/03 106/287.26 |
| 8,455,415 B2 * | 6/2013 | Patil | C07C 43/11 508/579 |
| 8,916,509 B2 * | 12/2014 | Maruyama | C10M 105/48 310/90 |
| 9,200,096 B2 * | 12/2015 | Patil | C08F 16/20 |
| 9,556,395 B2 * | 1/2017 | Kashani-Shirazi | C10M 145/32 |
| 9,561,992 B2 * | 2/2017 | Hayashi | C07C 43/275 |
| 2002/0002120 A1 | 1/2002 | Gahagan | |
| 2002/0019319 A1 | 2/2002 | Denpo et al. | |
| 2003/0050197 A1 | 3/2003 | Akao | |
| 2003/0153472 A1 | 8/2003 | Nagano et al. | |
| 2003/0166478 A1 | 9/2003 | Shimomura et al. | |
| 2006/0019840 A1 | 1/2006 | Kawahara et al. | |
| 2006/0040833 A1 | 2/2006 | Al-Akhdar et al. | |
| 2006/0045397 A1 | 3/2006 | Hirata et al. | |
| 2006/0166844 A1 | 7/2006 | Egawa et al. | |
| 2006/0171613 A1 * | 8/2006 | Shiraishi | C10M 105/18 384/13 |
| 2006/0199747 A1 | 9/2006 | Kamimura et al. | |
| 2007/0155632 A1 | 7/2007 | Hata et al. | |
| 2007/0221567 A1 | 9/2007 | Simmons et al. | |
| 2007/0281873 A1 * | 12/2007 | Okada | C10M 105/18 508/579 |
| 2008/0207804 A1 | 8/2008 | Gelbin et al. | |
| 2009/0011961 A1 | 1/2009 | Dong et al. | |
| 2010/0004151 A1 * | 1/2010 | Bush | C10M 107/34 508/564 |
| 2010/0266231 A1 * | 10/2010 | Sakaguchi | C10M 169/02 384/462 |
| 2011/0033145 A1 * | 2/2011 | Sakaguchi | C10M 169/02 384/470 |
| 2012/0283161 A1 | 11/2012 | Jung et al. | |
| 2013/0123553 A1 | 5/2013 | Sekiguchi et al. | |
| 2013/0345101 A1 * | 12/2013 | Imai | C10M 169/02 508/100 |

FOREIGN PATENT DOCUMENTS

| | | |
|---|---|---|
| JP | H03-200895 A | 9/1991 |
| JP | H03-200896 A | 9/1991 |
| JP | H04-20597 A | 1/1992 |
| JP | H04-57893 A | 2/1992 |
| JP | H04-505033 A | 9/1992 |
| JP | H06-41572 A | 2/1994 |
| JP | H06-172775 A | 6/1994 |
| JP | H06-200277 A | 7/1994 |
| JP | H06-228582 A | 8/1994 |
| JP | H06-299183 A | 10/1994 |
| JP | H06-345897 A | 12/1994 |
| JP | H08-109333 A | 4/1996 |
| JP | H08-311472 A | 11/1996 |
| JP | H09-31484 A | 2/1997 |
| JP | H10-324883 A | 12/1998 |
| JP | H11-286695 A | 10/1999 |
| JP | 2001-146598 A | 5/2001 |
| JP | 2002-038175 A | 2/2002 |
| JP | 2002-080879 A | 3/2002 |
| JP | 2002-348586 A | 12/2002 |
| JP | 2003-518159 A | 6/2003 |
| JP | 2004-161976 A | 6/2004 |
| JP | 2004-204002 A | 7/2004 |
| JP | 2005-232434 A | 9/2005 |
| JP | 2005-281474 A | 10/2005 |
| JP | 2006-064151 A | 3/2006 |
| JP | 2007-077244 A | 3/2007 |
| JP | 2007-186578 A | 7/2007 |
| JP | 2007204451 A | 8/2007 |
| JP | 2007-314764 A | 12/2007 |
| JP | 2008-001734 A | 1/2008 |
| JP | 4028982 B2 | 1/2008 |
| JP | 2008-189786 A | 8/2008 |
| JP | 2009-155432 A | 7/2009 |
| JP | 2009-263439 A | 11/2009 |
| JP | 2010-518237 A | 5/2010 |
| JP | 4466850 B2 | 5/2010 |
| JP | 2010-150562 A | 7/2010 |
| JP | 4769463 B2 | 9/2011 |
| KR | 2007-0043809 A | 4/2007 |
| KR | 2012-0125026 A | 11/2012 |
| KR | 2013-0047742 A | 5/2013 |
| WO | WO-01-059043 A1 | 8/2001 |
| WO | WO-01-090232 A2 | 11/2001 |
| WO | WO-04-018594 A1 | 3/2004 |
| WO | WO-2004-058928 A1 | 7/2004 |
| WO | WO-20040090082 A1 | 10/2004 |
| WO | WO-06-025253 A1 | 3/2006 |
| WO | WO-08-041508 A1 | 4/2008 |
| WO | WO-2010058021 A1 | 5/2010 |

OTHER PUBLICATIONS

International Search Report (in English and Japanese) and Written Opinion of the International Searching Authority (in Japanese) issued in PCT/JP2015/079666, dated Jan. 12, 2016.

International Preliminary Report on Patentability dated Aug. 15, 2017 issued in International Patent Application No. PCT/JP2015/079666.

* cited by examiner

LUBRICANT COMPOSITION, USE THEREOF AND ALIPHATIC ETHER COMPOUND

PRIORITY STATEMENT

This patent application is a U.S. national stage filing under 35 U.S.C. § 371 of International Application No. PCT/JP2015/079666 filed on 21 Oct. 2015, which claims priority to Japanese Patent Application No. 2015-023672 filed on 9 Feb. 2015. The entire disclosures of each of the above recited applications are incorporated herein by reference.

TECHNICAL FIELD

The present invention relates to a lubricant composition, use thereof, and an aliphatic ether compound. In particular, the present invention relates to (i) a lubricant composition having high moisture resistance and having physical properties such as low viscosity, low evaporability, low-temperature fluidity, and a high viscosity index, (ii) use thereof, and (iii) an aliphatic ether compound suitably used for such a lubricant composition.

BACKGROUND ART

The use of a lubricating oil composition having high viscosity leads to disadvantages such as an increased energy loss caused by a viscosity and an increased stirring loss of the lubricating oil composition. In order to overcome such disadvantages and achieve energy savings, low-viscosity lubricating oil compositions have been recently introduced in the field of lubricating oils. The low-viscosity lubricating oil compositions, however, suffer evaporation loss especially when used under a high-temperature atmosphere. In order to solve such a problem, there has been an increasing demand for a low-viscosity base oil that meets the requirement for low evaporability.

As lubrication base oils having low viscosity and suffering little evaporation, ester-based base oils are known. However, the ester-based base oils are poor in moisture resistance. That is, the ester-based base oils yield acids on hydrolysis with moisture in the air when they are used for a long term. The yielded acids may result in metallic corrosion. Further, the ester-based base oils, because of their high polarities, have adverse effects on organic materials such as rubbers and plastics.

In recent years, visual devices, audio devices, personal computers, etc. have been reduced in size and weight and increased in memory capacity, and increased in information processing speed. In keeping with this trend, fluid bearings have been developed and commercialized for their applications to rotating devices for driving magnetic disks and optical discs, such as FD, MO, mini disc, compact disc (CD), DVD and hard disk, employed in those electronic devices. The fluid bearing, which is made up of a sleeve and a rotation shaft facing each other via a lubricant, has no ball bearing. As such, the fluid bearing is suitable for reducing the size and weight of an electronic device and is excellent in, for example, silence and economical efficiency. A lubricating oil used for such a fluid bearing is required to have low viscosity even in a low-temperature range and to have (i) excellent low-temperature fluidity, (ii) a viscosity property of suffering little viscosity decrease even in a high-temperature range, and (iii) low evaporability.

Thus, in the field of lubricating oils, there has been an increasing demand for lubrication base oils and lubricating oil compositions both of which have high moisture resistance and physical properties such as low viscosity, low evaporability, low-temperature fluidity, and a high viscosity index.

In order to enhance performance of a lubricating oil, the mixing of an additive such as an antioxidant is generally performed. For example, Patent Literature 1 discloses that phenyl-α-naphthylamine, p,p'-dialkyl diphenylamine, and phosphate ester are mixed into a base oil in order to improve thermal stability, oxidative stability, resistance to sludge, lubricity, longevity, and water separability of a lubricant. Patent Literature 2 discloses a watch lubricating oil containing (i) an ether oil that serves as a base oil, (ii) an anti-wear agent, and (iii) an antioxidant, as a lubricating oil composition which is operable in the temperature range of −30° C. to 80° C., is free from change of properties over a long period of time, enables a life of watch battery to last long, and is favorable as a watch lubricating oil.

CITATION LIST

Patent Literature

[Patent Literature 1]
  Japanese Patent Application Publication Tokukai No. 2010-150562 (Publication Date: Jul. 8, 2010)
[Patent Literature 2]
  Publication of WO2001/059043 (Publication Date: Aug. 16, 2001)

SUMMARY OF INVENTION

Technical Problem

Unfortunately, when it comes to high moisture resistance and physical properties such as low viscosity, low evaporability, low-temperature fluidity, and a high viscosity index, the conventional lubricating oil compositions are insufficient.

The present invention has been attained in view of the above problem. It is an object of the present invention to provide (i) a lubricant composition having high moisture resistance and having physical properties such as low viscosity, low evaporability, low-temperature fluidity, and a high viscosity index, (ii) a technique of using thereof, and (iii) an aliphatic ether compound suitably used for such a lubricant composition.

Solution to Problem

In order to solve the above problem, a lubricant composition in accordance with the present invention is a lubricant composition including: an aliphatic ether compound that serves as a base oil; and an antioxidant, the antioxidant being made from at least alkylated phenylnaphthylamine and phosphite ester, wherein a sum of individual amounts of the alkylated phenylnaphthylamine and the phosphite ester, which are contained in the lubricant composition, is 3% to 8% by weight relative to a total amount of the base oil, and the alkylated phenylnaphthylamine and the phosphite ester are used in such a ratio that the alkylated phenylnaphthylamine and the phosphite ester account for 85% to 95% by weight and 5% to 15% by weight, respectively, of the sum of the individual amounts of the alkylated phenylnaphthylamine and the phosphite ester.

The lubricant composition in accordance with the present invention is preferably such that the aliphatic ether compound is an aliphatic ether compound having 8 to 300 carbon atoms in one molecule and having 1 to 150 oxygen atoms in one molecule.

The lubricant composition in accordance with the present invention is preferably such that the aliphatic ether compound is 2-(2-ethylhexyloxy)ethyl ether compound.

The lubricant composition in accordance with the present invention is preferably such that the aliphatic ether compound is at least one compound selected from the group consisting of compounds having respective structures represented by the following chemical formulae (1) to (10):

[Chem. 1]

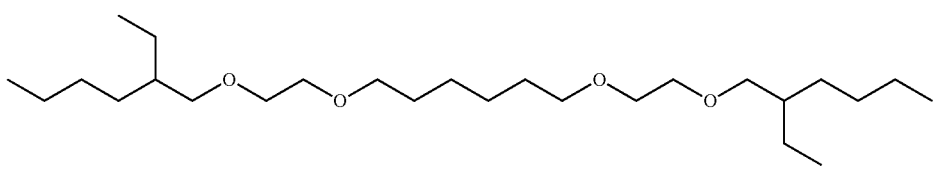

(1)

[Chem. 2]

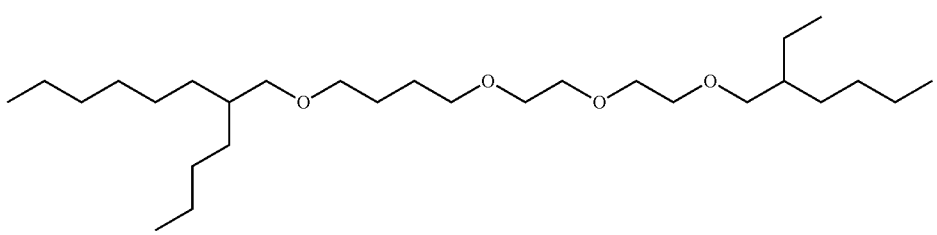

(2)

[Chem. 3]

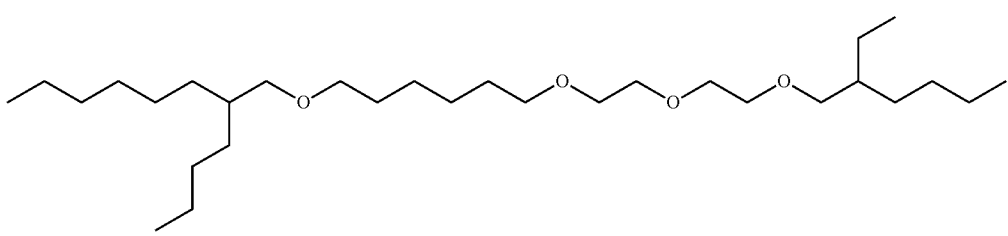

(3)

[Chem. 4]

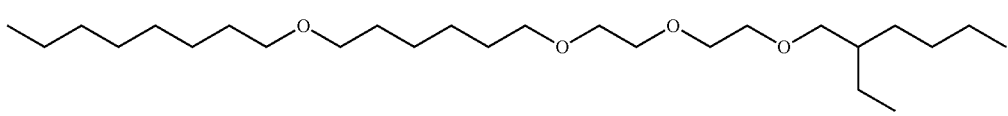

(4)

[Chem. 5]

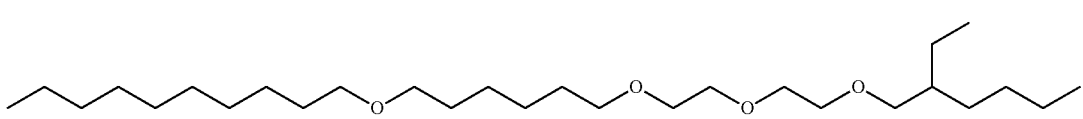

(5)

[Chem. 6]

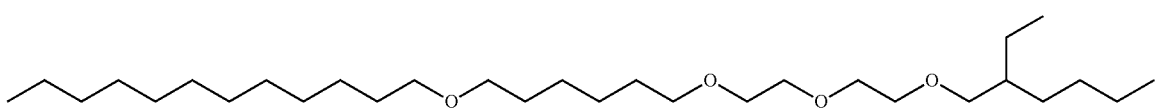

(6)

[Chem. 7]

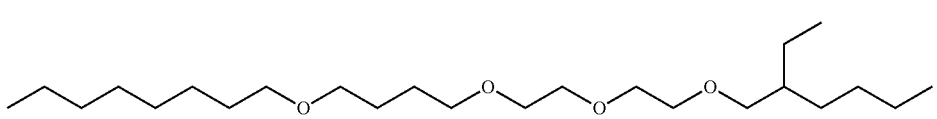

(7)

[Chem. 8]

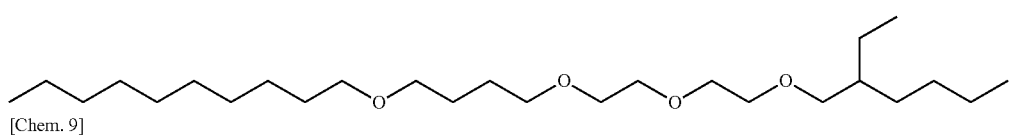

(8)

[Chem. 9]

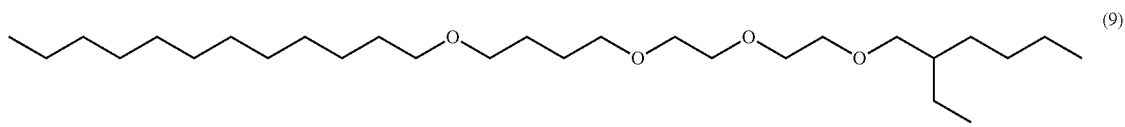

(9)

[Chem. 10]

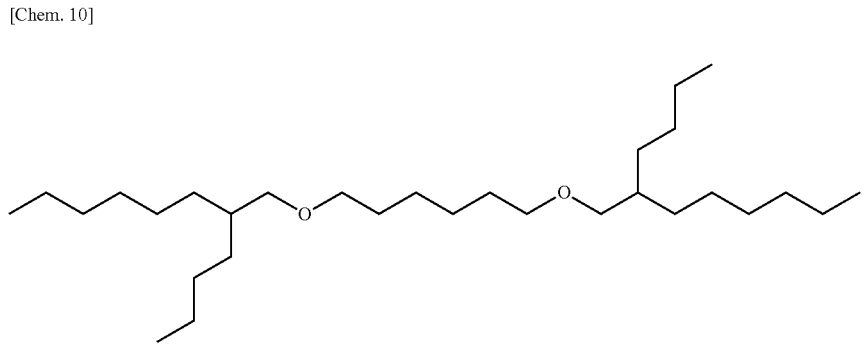

(10)

The lubricant composition in accordance with the present invention is preferably such that the alkylated phenylnaphthylamine is N-phenyl-dodecylnaphthalene-1-amine or N-phenyl-octylnaphthalene-1-amine.

The lubricant composition in accordance with the present invention is preferably such that the phosphite ester is 1,1,3-tris(2-methyl-4-ditridecylphosphite-5-t-butylphenyl) butane.

A bearing oil in accordance with the present invention preferably includes the lubricant composition.

A bearing in accordance with the present invention is preferably lubricated with use of the lubricant composition.

The bearing in accordance with the present invention is preferably such that the bearing is a fluid bearing or an impregnated bearing.

A motor in accordance with the present invention preferably includes the bearing.

A method for lubricating a bearing in accordance with the present invention preferably includes: lubricating a bearing with use of the lubricant composition.

Use of a lubricant composition in accordance with the present invention is preferably use for production of a grease.

A grease in accordance with the present invention preferably contains the lubricant composition.

A freezer oil in accordance with the present invention preferably contains the lubricant composition.

An aliphatic ether compound in accordance with the present invention preferably has a structure represented by any one of the following chemical formulae (1) to (9):

[Chem. 11]

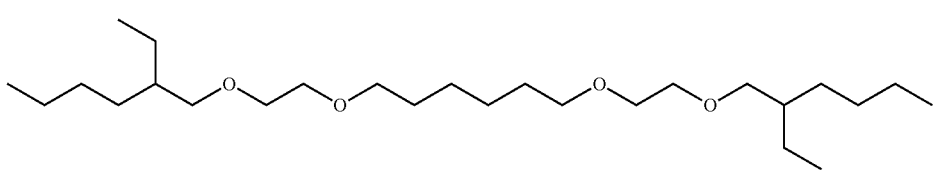

(1)

[Chem. 12]

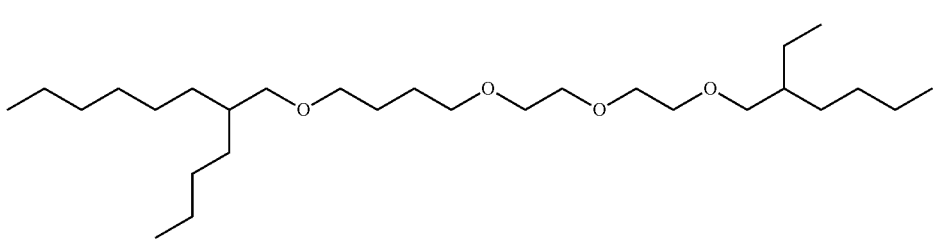

(2)

[Chem. 13]

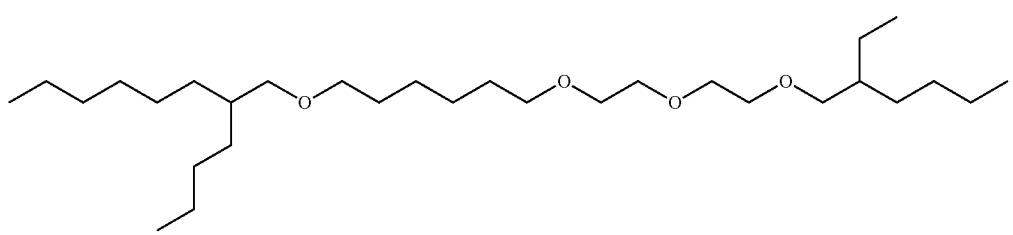

(3)

[Chem. 14]

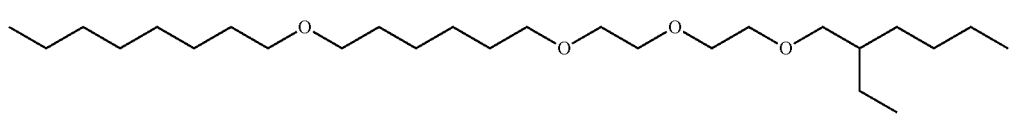

(4)

[Chem. 15]

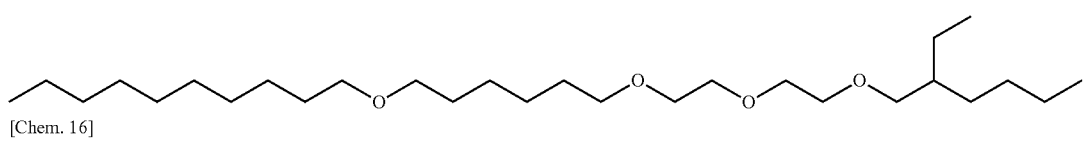

(5)

[Chem. 16]

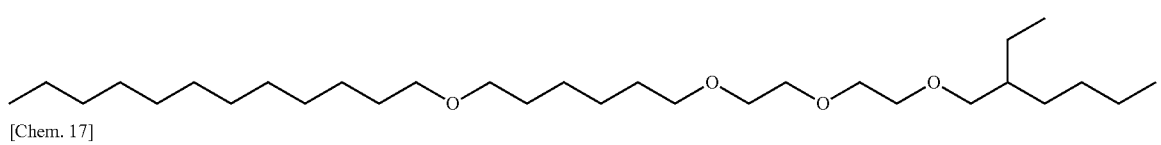

(6)

[Chem. 17]

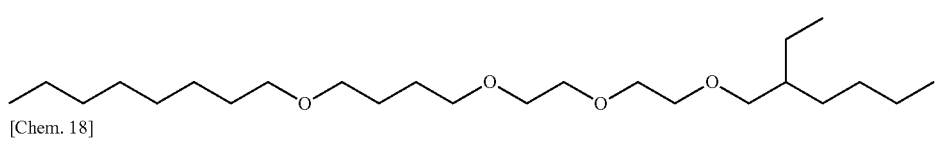

(7)

[Chem. 18]

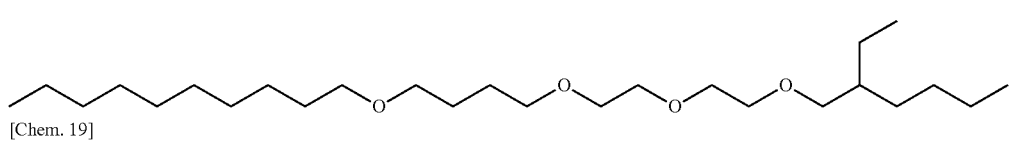

(8)

[Chem. 19]

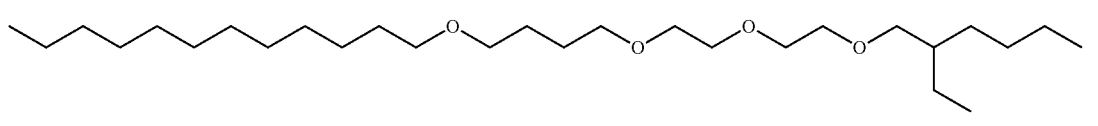

(9)

Advantageous Effects of Invention

The present invention enables achieving a lubricant composition having high moisture resistance and having physical properties such as low viscosity, low evaporability, low-temperature fluidity, and a high viscosity index.

DESCRIPTION OF EMBODIMENTS

Figure 1:
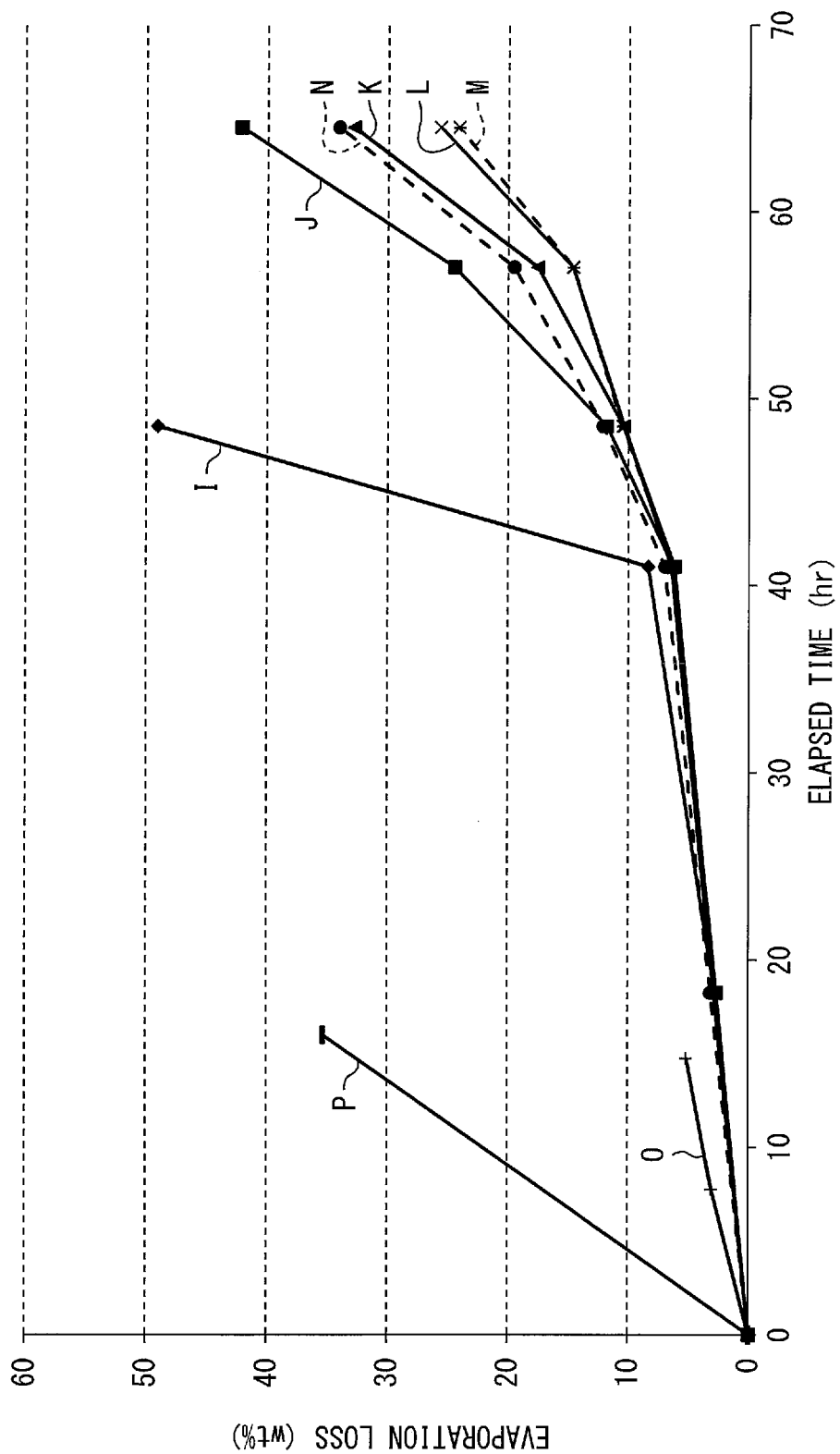
FIG. 1 is a graph showing results of measurement of evaporation losses of lubricant compositions prepared in Reference Examples 1 to 3 of the present invention and in Comparative Examples 1 to 5.

The following will describe an embodiment of the present invention in detail. Note, however, that the present invention is not limited to that embodiment. The present invention can be carried out in specific forms into which various modifications are incorporated within the scope set forth herein. All of the academic documents and patent literatures listed herein are incorporated by reference herein. Unless otherwise specified herein, "A to B" which indicates a numerical range means "not less than A and not more than B".

The present invention will be described below in the order of (1) a lubricant composition in accordance with the present invention, (2) use of a lubricant composition in accordance with the present invention, and (3) an aliphatic ether compound in accordance with the present invention.

(1) Lubricant Composition in Accordance with the Present Invention

The inventor of the present invention diligently studied in view of the above-described problem, and accomplished the present invention by finding that, with a lubricant composition containing (i) an aliphatic ether compound as a base oil and (ii) an antioxidant made from at least alkylated phenylnaphthylamine and phosphite ester, wherein a sum of individual amounts of the alkylated phenylnaphthylamine and the phosphite ester is a predetermined amount relative to the total amount of the base oil, and the alkylated phenylnaphthylamine and the phosphite ester are contained in a predetermined ratio, it is possible to provide a having high moisture resistance and having physical properties such as low viscosity, low evaporability, low-temperature fluidity, and a high viscosity index. Such a high degree of effect produced by the combined use of alkylated phenylnaphthylamine and phosphite ester is an effect exerted particularly when an aliphatic ether compound is used among other materials for a base oil.

[Base Oil]

The lubricant composition in accordance with the present invention uses an aliphatic ether compound as a base oil. The inventors of the present invention found that a combined use of alkylated phenylnaphthylamine and phosphite ester as an antioxidant achieves significantly reduced evaporation loss and found that such a high degree of effect is exerted particularly when an aliphatic ether compound is used among other materials for a base oil. That is, in a case where an aliphatic ether compound is used as a base oil, it is possible to achieve a high degree of effect produced by the combined use of alkylated phenylnaphthylamine and phosphite ester, i.e., a prominent effect of bringing about low evaporability.

An aliphatic ether compound is excellent in moisture resistance because it yields no acid on hydrolysis with moisture in the air. In addition, the aliphatic ether compound has lower polarity than an ester-based base oil and therefore has no adverse effect on organic materials such as rubbers and plastics.

An aliphatic ether used as a base oil in the present invention is not particularly limited. As such an aliphatic ether, an aliphatic ether commonly used as a base oil of a lubricant can be used suitably.

More preferably, the above-described aliphatic ether is an aliphatic ether having 8 to 300 carbon atoms in one molecule and having 1 to 150 oxygen atoms in one molecule. For a good balance of viscosity, low evaporability, and low-temperature fluidity, it is preferable that the number of carbon atoms in one molecule of the aliphatic ether and the number of oxygen atoms in one molecule of the aliphatic ether fall within the above-described ranges. Further, the above-described aliphatic ether has still more preferably 8 to 80 carbon atoms in one molecule and 1 to 40 oxygen atoms in one molecule, particularly preferably 8 to 60 carbon atoms in one molecule and 1 to 30 oxygen atoms in one molecule, and most preferably 8 to 40 carbon atoms in one molecule and 1 to 20 oxygen atoms in one molecule.

Especially, the above-described aliphatic ether is more preferably a 2-(2-ethylhexyloxy)ethyl ether compound having a structure represented by the following general formula (11):

[Chem. 20]

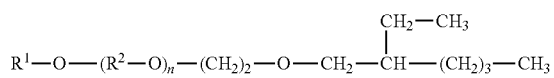

(11)

In the general formula (11), $R^1$ represents an alkyl group having 1 to 18 carbon atoms, $R^2$ represents an alkylene group having 2 to 18 carbon atoms, and n represents an integer of 1 to 6 on average. The structure represented by the general formula (11) contains one or more constitutional structures ($R^2$—O) that may be identical to each other or different from each other.

$R^1$ and $R^2$ may be linear or branched. $R^1$ having one or more carbon atoms, namely the ether compound having an alkoxyl group, rather than a hydroxyl group, at an end of a molecular structure, is preferable for a good separability from water, and $R^1$ having 18 or less carbon atoms is preferable for preventing significant impairment of low-temperature fluidity. Further, $R^2$ having two or more carbon atoms is preferable because an ether having such $R^2$ contains no acetal structure and thus leads to excellent moisture resistance and excellent resistance to lewis acids, and $R^2$ having 18 or less carbon atoms is preferable for preventing significant impairment of low-temperature fluidity. $R^1$ has more preferably 1 to 12 carbon atoms and still more preferably 2 to 8 carbon atoms. $R^2$ has more preferably 2 to 12 carbon atoms and still more preferably 2 to 8 carbon atoms. For a good balance of viscosity, low evaporability, and low-temperature fluidity, n is preferably 1 to 6 on average, more preferably 1 to 4 on average, and still more preferably 1 to 2 on average.

As a more specific example, the aliphatic ether is more preferably at least one compound selected from the group consisting of compounds having respective structures represented by the above-described chemical formulae (1) to (10). Note that the compound having the structure represented by the chemical formula (1) can be referred to herein as compound 1, the compound having the structure represented by the chemical formula (2) can be referred to herein as compound 2, the compound having the structure represented by the chemical formula (3) can be referred to herein as compound 3, the compound having the structure represented by the chemical formula (4) can be referred to herein as compound 4, the compound having the structure represented by the chemical formula (5) can be referred to herein as compound 5, the compound having the structure represented by the chemical formula (6) can be referred to herein as compound 6, the compound having the structure represented by the chemical formula (7) can be referred to herein as compound 7, the compound having the structure represented by the chemical formula (8) can be referred to herein as compound 8, the compound having the structure represented by the chemical formula (9) can be referred to herein as compound 9, and the compound having the structure represented by the chemical formula (10) can be referred to herein as compound 10.

As the base oil used in the present invention, the above-described aliphatic ethers may be used singly or in combination of two or more thereof.

Further, the lubricant composition in accordance with the present invention contains the aliphatic ether compound as the base oil, but may further contain a small amount of another base oil, which is not the aliphatic ether compound, provided that the other base oil does not adversely affect the advantageous effect of the present invention. The other base oil, which is not the aliphatic ether compound, accounts for preferably not more than 10% by weight, and more preferably not more than 5% by weight, of the total amount of the base oils.

A method for producing the aliphatic ether is not limited to a particular one. The aliphatic ether can be obtained by any production method. For example, the aliphatic ether can be produced by polymerization of alkylene oxide such as ethylene oxide or propylene oxide. Alternatively, the aliphatic ether can be produced by etherizing a hydroxyl group at an end of the polyalkylene oxide, which has been obtained by the above-described method, through substitution reaction of the polyalkylene oxide with use of alkyl chloride.

Alternatively, the above-described aliphatic ether can be a commercially available product. For example, the following commercially available products: ADEKA CARPOL M-series available from ADEKA Corporation; NOIGEN XL series such as NOIGEN XL-40, NOIGEN TDS series such as NOIGEN TDS-30, NOIGEN TDX series such as NOIGEN TDX-50, NOIGEN SD series such as NOIGEN SD-60, NOIGEN LP series such as NOIGEN LP-100, and ANTI-FROTH F-233, which are available from Dai-ichi Kogyo Seiyaku Co., Ltd.; and the like products, can be suitably used as the aliphatic ether.

Methods for producing the compounds 1 to 10 are not limited to particular methods. For example, the compounds 1 to 10 can be produced, by way of example, by the existing synthesis method described in the publication of WO2006/025253, etc.

More specifically, the compound 1 can be obtained by, for example, etherification reaction of 2-ethylhexyloxy ethyl alcohol and 1,6-dichlorohexane.

For example, the compound 3 can be obtained by the following method. That is, etherification reaction of 2-(2-ethylhexyloxy)ethyl alcohol and 1,6-dichlorohexane is performed to synthesize 6-[2-(2-ethylhexyloxy)ethoxy]-hexyl chloride, which is isolated and purified as an intermediate by reduced-pressure distillation. Thereafter, etherification reaction of the intermediate and 2-butyloctanol is performed to obtain the compound 3.

For example, the compounds 4, 5, and 6 can be each synthesized by a method similar to the method for synthesizing the compound 3, except that etherification reaction is performed using a corresponding alcohol instead of 2-butyloctanol.

For example, the compounds 2, 7, 8 and 9 can be each synthesized by a method similar to the method for synthesizing the compound 3, in such a manner that etherification reaction is performed using 1,4-dichlorohexane instead of 1,6-dichlorohexane to synthesize 4-[2-(2-ethylhexyloxy)ethoxy]-butyl chloride, which is isolated and purified as an intermediate by reduced-pressure distillation, and etherification reaction of the intermediate with a corresponding alcohol is then performed to obtain each of the compounds 2, 7, 8 and 9.

Note that methods for synthesizing the compounds 1 to 10 are not limited to the above-described methods. After the above-described etherification reaction is sufficiently carried out, a product can be purified as appropriate by a known method (e.g., reduced-pressure distillation or separation through silica gel column chromatography) to obtain each of the compounds 1 to 10 that can be used as a base oil of a lubricant.

[Antioxidant]

The lubricant composition in accordance with the present invention contains (i) an aliphatic ether compound which serves as a base oil and (ii) a combination of at least alkylated phenylnaphthylamine and phosphite ester which combination serves as an antioxidant, wherein a sum of individual amounts of the alkylated phenylnaphthylamine and the phosphite ester is a predetermined amount relative to the total amount of the base oil, and the alkylated phenylnaphthylamine and the phosphite ester are contained in a predetermined ratio.

A combined use of alkylated phenylnaphthylamine and phosphite ester, as the antioxidant, creates a synergistic effect and thus achieves the effect of promoting low evaporability. Further, the combined use of alkylated phenylnaphthylamine and phosphite ester also achieves the effect of further prolonging the duration of effectiveness for antioxidation.

<Alkylated Phenylnaphthylamine>

The alkylated phenylnaphthylamine used in the present invention, namely alkyl-substituted phenylnaphthylamine, is not limited to a particular compound, provided that at least one of a phenyl group and a naphthyl group in phenylnaphthylamine is substituted with an alkyl group. As the alkylated phenylnaphthylamine used in the present invention, for example, alkylated phenyl-α-naphthylamine having a structure represented by the following general formula (12):

[Chem. 21]

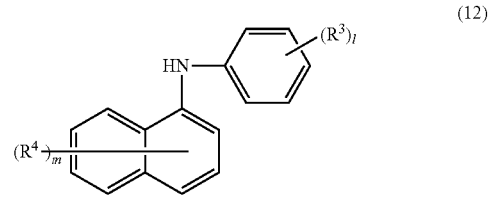

or alkylated phenyl-β-naphthylamine having a structure represented by the following general formula (13):

[Chem. 22]

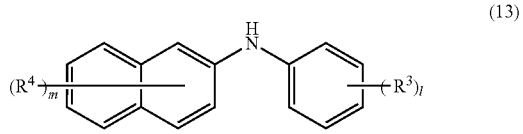
(13)

can be suitably used.

In the general formulae (12) and (13), $R^3$ and $R^4$ independently represents a linear or branched alkyl group having 1 to 18 carbon atoms, 1 is an integer of 0 to 5, m is an integer of 0 to 7, and 1+m is not less than 1. $R^3$ and $R^4$ each having an alkyl group having 4 to 18 carbon atoms are preferable for achieving a high degree of solubility in an aliphatic ether compound and for reducing the tendency of the alkylated phenylnaphthylamine itself to evaporate.

More specifically, examples of $R^3$ include alkyl groups such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, and an octadecyl group. These alkyl groups may be linear or branched. $R^3$ is more preferably an alkyl group having 4 to 18 carbon atoms and particularly preferably an alkyl group having 4 to 12 carbon atoms. In a case where the number of substituents, 1, is 2 or more, two or more $R^3$ may be identical to each other or different from each other. Further, a substitution position of $R^3$ is not limited to a particular position. The number of substituents, 1, is an integer of 0 to 5, more preferably 0 to 2, and still more preferably 0 to 1.

Further, examples of $R^4$ include alkyl groups such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, and an octadecyl group. These alkyl groups may be linear or branched. $R^4$ is more preferably an alkyl group having 4 to 18 carbon atoms and particularly preferably an alkyl group having 4 to 12 carbon atoms. In a case where the number of substituents, m, is 2 or more, two or more $R^4$ may be identical to each other or different from each other. Further, a substitution position of $R^4$ is not limited to a particular position. The number of substituents, m, is an integer of 0 to 7, more preferably 0 to 2, and still more preferably 0 to 1.

As the compound represented by the general formula (12) or (13), alkylated phenylnaphthylamine having a structure such that $R^3$ is an alkyl group having 4 to 12 carbon atoms, 1 is an integer of 0 to 1, $R^4$ is an alkyl group having 4 to 12 carbon atoms, m is an integer of 0 to 1, and 1+m is not less than 1, can be used particularly suitably. Specific examples of such alkylated phenylnaphthylamine include N-phenyl-dodecylnaphthalene-1-amine, N-phenyl-octylnaphthalene-1-amine, N-phenyl-butylnaphthalene-1-amine, N-dodecyl-phenyl-dodecylnaphthalene-1-amine, N-octylphenyl-octylnaphthalene-1-amine, N-dodecylphenyl-naphthalene-1-amine, and N-octylphenyl-naphthalene-1-amine.

The alkylated phenylnaphthylamine can be a commercially available product. As the alkylated phenylnaphthylamine, for example, IRGANOX L06 available from BASF Corporation and Naugalube APAN available from Chemtura Corporation can be suitably used.

<Phosphite Ester>

The phosphite ester used in the present invention is not limited to a particular one, provided that it is an ester of phosphorous acid. As the phosphite ester used in the present invention, for example, a tertiary phosphite having a structure represented by the following general formula (14):

[Chem. 23]

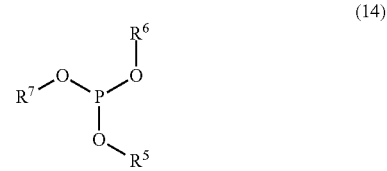
(14)

or phosphite ester having a structure represented by the following general formula (16):

[Chem. 24]

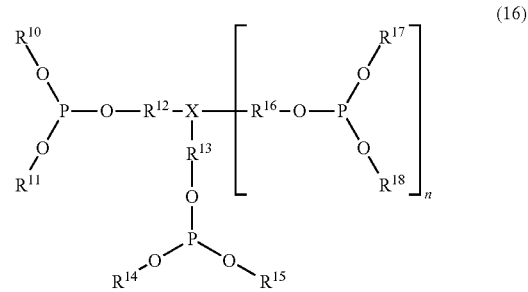
(16)

can be suitably used.

In the general formula (14), $R^5$, $R^6$, and $R^7$ independently represent an aliphatic hydrocarbon group having 1 to 18 carbon atoms or an aromatic hydrocarbon group having 4 to 30 carbon atoms.

In the general formula (16), $R^{10}$, $R^{11}$, $R^{12}$, $R^{13}$ $R^{14}$, $R^{15}$, $R^{16}$, $R^{17}$ and $R^{18}$ independently represent an aliphatic hydrocarbon group having 1 to 18 carbon atoms or an aromatic hydrocarbon group having 4 to 30 carbon atoms, X represents a divalent, trivalent, or tetravalent aliphatic hydrocarbon group having 1 to 18 carbon atoms, and n represents 0, 1, or 2.

In a case where $R^5$, $R^6$, $R^7$, $R^{10}$, $R^{11}$, $R^{14}$, $R^{15}$, $R^{17}$, and $R^{18}$ are aliphatic hydrocarbon groups, examples of such aliphatic hydrocarbon groups include alkyl groups such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, and an octadecyl group. These alkyl groups may be linear or branched. The aliphatic hydrocarbon groups are not limited to the above-described alkyl groups. Alternatively, the aliphatic hydrocarbon groups may be unsaturated aliphatic hydrocarbon groups. In a case where $R^{12}$, $R^{13}$, and $R^{16}$ are aliphatic hydrocarbon groups, examples of such aliphatic hydrocarbon groups include alkylene groups each having 1 to 18 carbon atoms. Those alkylene groups may be linear or branched. The aliphatic hydrocarbon groups are not limited to the above-described alkylene groups. Alternatively, the aliphatic hydrocarbon groups may be unsaturated aliphatic hydrocarbon groups.

In a case where $R^5$, $R^6$, $R^7$, $R^{10}$, $R^{11}$, $R^{14}$, $R^{15}$, $R^{17}$, and $R^{18}$ are aromatic hydrocarbon groups, examples of such aromatic hydrocarbon groups include a phenyl group, an alkylated phenyl group, and the like. The alkylated phenyl group is a phenyl group in which at least 1 to 5 hydrogen atoms on a benzene ring are substituted with a linear or branched alkyl group having 1 to 18 carbon atoms. A position of the alkyl substitution on the benzene ring is not limited to a particular position. In a case where the number of substituents is 2 or more, two or more alkyl groups may be identical to each other or different from each other. In a case where $R^{12}$, $R^{13}$, and $R^{16}$ are aromatic hydrocarbon groups, examples of such aromatic hydrocarbon groups include a phenylene group, an alkylated phenylene group, and the like. The alkylated phenylene group is a phenylene group in which at least 1 to 4 hydrogen atoms on a benzene ring are substituted with a linear or branched alkyl group having 1 to 18 carbon atoms. A position of the alkyl substitution on the benzene ring is not limited to a particular position. In a case where the number of substituents is 2 or more, two or more alkyl groups may be identical to each other or different from each other.

X is not limited to a particular one, provided that it is a divalent, trivalent, or tetravalent aliphatic hydrocarbon group having 1 to 18 carbon atoms. The aliphatic hydrocarbon group may be a saturated aliphatic hydrocarbon group or an unsaturated aliphatic hydrocarbon group and may be linear or branched. More preferably, the aliphatic hydrocarbon group is a branched or linear saturated aliphatic hydrocarbon group having 1 to 6 carbon atoms. Further, $R^{12}$, $R^{13}$, and $R^{16}$ may be attached to any carbon atom on the aliphatic hydrocarbon group.

More specific examples of the phosphite ester having the structure represented by the general formula (14) include triphenyl phosphite, trisnonylphenylphosphite, tricresyl phosphite, triethyl phosphite, tris(2-ethylhexyl)phosphite, tridecyl phosphite, trilauryl phosphite, tris(tridecyl)phosphite, trioleyl phosphite, diphenyl mono(2-ethylhexyl)phosphite, diphenyl monodecyl phosphite, diphenyl mono(tridecyl)phosphite, tristearyl phosphite, tris(2,4-di-tert-butylphenyl)phosphite, and the like.

More specific examples of the phosphite ester having the structure represented by the general formula (16) include 1,1,3-tris(2-methyl-4-ditridecylphosphite-5-t-butylphenyl) butane (ADK STAB 522A available from ADEKA Corporation), a mixture of tetraphenyl tetra(tridecyl)pentaerythritol tetraphosphite and bis(2-ethylhexyl)phthalate, tetra(C12-C15 alkyl)-4,4'-isopropylidene diphenyl diphosphite, and the like.

Not only the phosphite esters represented by the general formulae (14) and (16), but also trilauryl trithio phosphite, tetraphenyl dipropyleneglycol diphosphite, a mixture of bis(tridecyl)pentaerythritol diphosphite and bis(nonylphenyl)pentaerythritol diphosphite, bis(decyl)pentaerythritol diphosphite, bis(tridecyl)pentaerythritol diphosphite, distearyl pentaerythritol diphosphite, hydrogenated bisphenol A pentaerythritol phosphite polymer, hydrogenated bisphenol A phosphite polymer, and the like can be suitably used as the phosphite ester in the present invention.

As the above-described phosphite ester, a commercially available product can be used. For example, JP-360, JP-351, JP-3CP, JP-302, JP-308E, JP-310, JP-312L, JP-333E, JP-318-0, JPM-308, JPM-311, JPM-313, JPS-312, JP-202, JPE-208, JP-212, JP-213D, JP-218-OR, JP-260, JPP-100, JPP-613M, JA-805, JPP-88, JPE-10, JPE-13R, JP-318E, JPP-2000T, JP-650, JPH-3800, and HBP available from Johoku Chemical Co., Ltd.; ADK STAB 522A available from ADEKA Corporation; and the like can be suitably used.

The above-described phosphite ester is more preferably phosphite ester having a molecular weight of not less than 300 and having low evaporability. A phosphite ester having a molecular weight that falls within the above range is preferable for reducing the tendency of the phosphite ester itself to evaporate. The above-described phosphite ester is still more preferably phosphite ester having a molecular weight in a range of 400 to 1000, and particularly preferably phosphite ester having a molecular weight in a range of 500 to 800.

[Amount of Antioxidant to be Added]

A sum of individual amounts of the alkylated phenylnaphthylamine and the phosphite ester, which are contained in the lubricant composition of the present invention, is preferably 3% to 8% by weight relative to the total amount of the base oil.

In a case where the sum of the individual amounts of the alkylated phenylnaphthylamine and the phosphite ester is 3% to 8% by weight relative to the total amount of the base oil, it is possible to achieve the effects of suffering less evaporation loss of the lubricant composition and of having a large amount of time elapsed before the evaporation loss starts increasing with a steep gradient.

In a case where the sum of the individual amounts of the alkylated phenylnaphthylamine and the phosphite ester is not more than 8% by weight relative to the total amount of the base oil, it is possible to obtain a lubricant composition that is capable of reducing a tendency to increase its viscosity and has an excellent thermal stability.

Further, the alkylated phenylnaphthylamine and the phosphite ester are contained in the lubricant composition preferably in such a ratio that the alkylated phenylnaphthylamine and the phosphite ester account for 85% to 95% by weight and 5% to 15% by weight, respectively, of the sum of the individual amounts of the alkylated phenylnaphthylamine and phosphite ester.

A lubricant composition containing the alkylated phenylnaphthylamine and the phosphite ester in a ratio that falls within the above range achieves prominent effects of suffering less evaporation loss of the lubricant composition and of further prolonging the duration of effectiveness for antioxidation.

Further, the lubricant composition in accordance with the present invention uses, as an antioxidant, alkylated phenylnaphthylamine and phosphite ester, but may further contain a small amount of another antioxidant, which is not alkylated phenylnaphthylamine or phosphite ester, provided that the other antioxidant does not adversely affect the advantageous effect of the present invention. The other antioxidant, which is not alkylated phenylnaphthylamine or phosphite ester, accounts for preferably not more than 10% by weight, and more preferably not more than 5% by weight, of the sum of the individual amounts of the antioxidants.

[Other Additives]

The lubricant composition in accordance with the present invention may contain various additives, as well as the base oil and the antioxidant, in order to further improve practical properties. Examples of the additives include metal deactivators, corrosion inhibitors, conductivity imparting agents, and the like.

As the metal deactivators, benzotriazole, 5-methyl-1H-benzotriazole, 1-dioctylaminomethylbenzotriazole, 1-dioctylaminomethyl-5-methylbenzotriazole, 2-(5'-methyl-2'-hydroxyphenyl)benzotriazole, 2-[2'-hydroxy-3',5'-bis(α,α-dimethylbenzyl)phenyl]-2H-benzotriazole, 2-(3',5'-di-t- butyl-2'-hydroxyphenyl)benzotriazole, 2-(3'-t-butyl-5'-methyl-2'-hydroxyphenyl)-5-chlorobenzotriazole, 2-(3',5'-di-t-butyl-2'-hydroxyphenyl)-5-chlorobenzotriazole, 2-(3',5'-di-t-amyl-2'-hydroxyphenyl)benzotriazole, 2-(5'-t-butyl-2'-hydroxyphenyl)benzotriazole, 2-(2'-hydroxy-5'-methylphenyl)benzotriazole, 2-(2'-hydroxy-5'-t-octylphenyl)benzotriazole, and 2-[2'-hydroxy-3'-(3",4",5",6"-tetrahydrophthalidemethyl)-5'-methylphenyl] benzotriazole can be suitably used.

As the corrosion inhibitors, the following compounds: alkyl or alkenyl succinic acid derivatives such as dodecenyl succinic acid half ester, octadecenyl succinic anhydride, and dodecenyl succinamide; polyhydric alcohol partial esters such as sorbitan monooleate, glycerin monooleate, and pentaerythritol monooleate; metal sulfonates such as Ca-petroleum sulfonate, Ca-alkyl benzene sulfonate, Ba-alkyl benzene sulfonate, Mg-alkyl benzene sulfonate, Na-alkyl benzene sulfonate, Zn-alkyl benzene sulfonate, and Ca-alkyl naphthalene sulfonate; amines such as rosin amine and N-oleyl sarcosine; and the like can be suitably used.

As the conductivity imparting agents, alkylnaphthalene-sulfonic acid esters, sorbitan esters of fatty acids, polyoxy-ethylene sorbitan esters of fatty acids, polyoxyethylene alkyl ethers, polyoxyethylene alkenyl ethers, and the like can be suitably used.

In the present invention, the lubricant composition contains one or more types of additives which are selected from the above-listed additives and which individually account for 0.01% to 1% by weight of the total amount of the lubricant composition. Such an arrangement enables further improved practical properties of the lubricant composition of the present invention.

[Lubricant Composition]

With the above arrangement, the lubricant composition in accordance with the present invention has physical properties, such as low viscosity, low evaporability, low-temperature fluidity, and a high viscosity index, induces less metallic corrosion that can occur on hydrolysis, and has less adverse effect on an organic material. In addition, the lubricant composition in accordance with the present invention is excellent in that effectiveness of the antioxidant lasts for a long duration of time.

The lubricant composition in accordance with the present invention has a kinetic viscosity at 40° C. (hereinafter also referred to as "40° C. kinetic viscosity") preferably in a range of 4 cSt to 1000 cSt, and more preferably in a range of 6 cSt to 30 cSt. A lubricant composition having a 40° C. kinetic viscosity that falls within the above range can serve as a bearing oil especially excellent in lubricity and energy-saving.

Further, in a case where the lubricant composition in accordance with the present invention has a viscosity index of preferably not less than 80 and more preferably not less than 110 and has a pour point of preferably not higher than −5° C. and more preferably not higher than −40° C., the lubricant composition can be used as a bearing lubricant that is especially excellent in low-temperature viscosity property.

Note that the "kinetic viscosity of the lubricant composition at 40° C.", "viscosity index", and "pour point" herein can be measured by methods provided in Examples, which will be described later.

(2) Use of Lubricant Composition in Accordance with the Present Invention

[Bearing Oil]

The lubricant composition of the present invention can be used as a bearing oil for any bearing to be lubricated with use of a lubricant. Thus, the present invention includes a bearing oil that contains the lubricant composition of the present invention. For example, the lubricant composition of the present invention can be suitably used as a bearing oil for any bearing that includes a shaft member and a bearing member (sleeve member) and is arranged such that (i) the shaft member and the bearing member are rotatably fitted with each other via a minute gap between them, (ii) a working fluid (bearing oil) is contained in the minute gap so as to form a lubricating film and (iii) the shaft member and the bearing member relatively slide via the lubricating film. Such a bearing is generally called a "slide bearing".

The lubricant composition of the present invention can also be suitably used as a bearing oil for a fluid bearing (fluid dynamic bearing or static pressure bearing) or as a bearing oil for an impregnated bearing (also called "oil-impregnated bearing").

[Bearing]

The bearing in accordance with the present invention is lubricated with use of the above-described lubricant composition of the present invention. The bearing in accordance with the present invention can have any configuration, provided that the bearing is to be lubricated with use of the above-described lubricant composition of the present invention. Note that "to be lubricated with use of the lubricant composition of the present invention" intends that members facing each other via the lubricant composition of the present invention relatively slide via the lubricant composition of the present invention. Examples of the bearing include, for example, a fluid bearing and an impregnated bearing.

The "fluid bearing" can have any configuration, provided that it is a publicly known fluid bearing which (i) includes a shaft member (or a thrust plate) and a sleeve member but does not have a mechanism such as a ball bearing and (ii) is arranged such that: the shaft member (or the thrust plate) and the sleeve member are rotatably fitted with each other via a minute gap between them; a working fluid (lubricant composition) is contained in the minute gap so as to form a lubricating film; and the shaft member (or the thrust plate) and the sleeve member are held via the lubricating film so as not to be in direct contact with each other.

Of such fluid bearings, the following are particularly called "fluid dynamic bearings": a fluid bearing in which a shaft member and/or a sleeve member have/has a dynamic pressure generating groove(s), and the shaft member is supported by dynamic pressure; a fluid bearing which includes a thrust plate so that dynamic pressure is generated in a direction perpendicular to a rotation axis of a shaft member; and the like. The bearing of the present invention also encompasses such fluid dynamic bearings.

In the fluid dynamic bearings described above, no dynamic pressure is generated while the shaft member (or the thrust plate) is not rotating. Therefore, while the shaft member (or the thrust plate) is not rotating, the sleeve member and the shaft member (or the thrust plate) are partly or fully in contact with each other. On the other hand, while the shaft member (or the thrust plate) is rotating, dynamic pressure is generated by the rotation, and thus the sleeve member and the shaft member (or the thrust plate) separate from each other. That is, in the fluid dynamic bearings, the sleeve member and the shaft member (or the thrust plate) constantly repeat contacting with each other and separating from each other. According to conventional fluid dynamic bearings, (i) metal wear may occur between a sleeve member and a shaft member (or a thrust plate), or (ii) seizure may occur because the sleeve member and the shaft member (or the thrust plate) temporarily contact with each other while the shaft member (or the thrust plate) is rotating. Furthermore, since conventional fluid dynamic bearings are likely to accumulate static electricity, important electronic components such as a magnetic disk may suffer electrostatic destruction. On the other hand, the fluid bearings in accordance with the present invention are lubricated with use of the lubricant composition of the present invention. This reduces the possibility of such metal wear and seizure, and also reduces the likelihood that static electricity is accumulated between the sleeve member and the shaft member (or the thrust plate).

The "impregnated bearing" can have any configuration, provided that it is a publicly known impregnated bearing (oil-impregnated bearing) that includes a porous shaft member which is made of sintered metal, synthetic resin, or the like and which is impregnated with the lubricant of the present invention.

In conventional impregnated bearings, (i) metal wear may occur between a bearing member and a shaft member or (ii) seizure may occur because the bearing member and the shaft member temporarily contact with each other while the shaft member is rotating. Furthermore, since the conventional impregnated bearings are likely to accumulate static electricity, important electronic components such as a magnetic disk may suffer electrostatic destruction. On the other hand, the impregnated bearing in accordance with the present invention is lubricated with use of the lubricant composition of the present invention. This reduces the possibility of such metal wear and seizure, and also reduces the likelihood that static electricity is accumulated between the bearing member and the shaft member.

As described earlier, the lubricant composition of the present invention is capable of having high moisture resistance, and meeting physical properties such as low viscosity, low evaporability, low-temperature fluidity, and a high viscosity index in a well-balanced manner, as compared to conventional bearing lubricants. Accordingly, the bearing of the present invention, which is lubricated with use of the lubricant composition of the present invention as a working fluid, can be used as a bearing that (i) achieves long-term stability and durability, etc. even in a case where the bearing is rotated at high speed and (ii) is excellent in energy-saving. As such, the bearing of the present invention can be effectively used as a bearing for use in a rotating device, etc. of an electronic device, such as an audio-visual device and a personal computer, which has been required to decrease in size and weight and to increase in memory capacity and information processing speed.

[Motor]

A motor in accordance with the present invention includes a bearing of the present invention. The motor in accordance with the present invention may have any configuration, provided that it includes the bearing of the present invention. Note that the bearing of the present invention has been described in the earlier section [Bearing], and the description thereof is therefore omitted here.

Examples of the motor in accordance with the present invention include those provided in known electronic devices such as personal computers, audio devices, visual devices, and car navigation systems.

The motor in accordance with the present invention includes a bearing which is lubricated with use of a lubricant composition of the present invention. The motor in accordance with the present invention is, therefore, less likely to suffer metal wear and seizure and less likely to accumulate static electricity between a bearing member and a shaft member, as compared with conventional motors. As such, the motor in accordance with the present invention achieves long-term stability and durability, etc. even in the case where the bearing is rotated at high speed, and thus increases the lifetime of the motor. Furthermore, the motor in accordance with the present invention can be used as a motor particularly excellent in energy-saving in the case where the bearing is rotated at high speed, as compared to the conventional motors.

[Method for Lubricating Bearing]

A method for lubricating a bearing in accordance with the present invention is characterized by lubricating a bearing of the present invention with use of a lubricant composition of the present invention. Note that the lubricant composition of the present invention and the bearing of the present invention have been described in the earlier sections [(1) Lubricant composition in accordance with the present invention] and [Bearing], respectively, and the descriptions thereof are therefore omitted here.

As described earlier, the lubricant composition of the present invention is capable of having high moisture resistance and meeting physical properties such as low viscosity, low evaporability, low-temperature fluidity, and a high viscosity index in a well-balanced manner, as compared to the conventional bearing lubricants. Therefore, by using the lubricant composition of the present invention as a working fluid for lubrication of a bearing, it is possible to achieve long-term stability and durability, etc. even in the case where the bearing is rotated at high speed, and it is thus possible to increase the lifetime of the bearing. Further, it is possible to cause the bearing to be more power-saving.

[Grease]

A grease in accordance with the present invention contains a lubricant composition of the present invention. The present invention also includes use of the lubricant composition for production of a grease. Note that the lubricant composition of the present invention has been described in the earlier section [(1) Lubricant composition in accordance with the present invention], and the description thereof is therefore omitted here.

The grease in accordance with the present invention contains the lubricant composition of the present invention in an amount of preferably not less than 50% by weight, and further preferably not less than 95% by weight, relative to the total weight of the grease.

The grease in accordance with the present invention may be solid or semisolid at room temperature. Further, the grease in accordance with the present invention usually contains a thickener in an amount that is required for the grease to have a desired consistency. Usually, the thickener is contained in an amount of, for example, 10% to 40% by weight relative to the total weight of the grease.

The "thickener" may be one that is usually used in grease. Examples of the thickener include, but are not limited to, lithium soap, calcium soap, sodium soap, and aluminum soap.

The grease in accordance with the present invention may further contain additives such as antioxidants, extreme-pressure agents, and/or corrosion inhibitors according to need. Each of these additives, when contained in the grease, accounts for 0.1% to 5% by weight of the total weight of the grease. This makes it possible to achieve better practical properties of the grease.

The grease in accordance with the present invention is not particularly limited as to its application, but it is suitable for use as a grease for a bearing, particularly as a grease for a fluid bearing or a grease for an impregnated bearing.

A method for producing the grease in accordance with the present invention is not particularly limited. The grease in accordance with the present invention can be produced by a common grease production method.

Since the grease in accordance with the present invention contains as a base oil the lubricant composition of the present invention, the grease can be used as a grease that more certainly meets all the properties such as energy-saving, high moisture resistance, low evaporability, and low-temperature viscosity property in a well-balanced manner, as compared to conventional greases.

[Freezer Oil]

The freezer oil in accordance with the present invention contains the lubricant composition of the present invention. Note that the lubricant composition of the present invention has been described in the earlier section [(1) Lubricant composition in accordance with the present invention], and the description thereof is therefore omitted here.

The freezer oil in accordance with the present invention contains the lubricant composition of the present invention in an amount of preferably not less than 80% by weight, and more preferably not less than 90% by weight relative to the total weight of the freezer oil.

The freezer oil in accordance with the present invention may further contain additives such as metal deactivators, corrosion inhibitors, and/or conductivity imparting agents according to need. Each of these additives, when contained in the freezer oil, accounts for 0.01% to 5% by weight of the total weight of the freezer oil. This makes it possible to achieve better practical properties of the freezer oil.

A method for producing the freezer oil in accordance with the present invention is not particularly limited. The freezer oil in accordance with the present invention can be produced by a common freezer oil production method.

Since the freezer oil in accordance with the present invention contains as a base oil the lubricant composition of the present invention, the freezer oil can be used as a freezer oil that more certainly meets all the properties such as energy-saving, high moisture resistance, low evaporability, and low-temperature viscosity property in a well-balanced manner, as compared with conventional freezer oils.

(3) Aliphatic Ether Compound in Accordance with the Present Invention

An aliphatic ether compound that can be suitably used in the lubricating oil composition in accordance with the present invention includes a novel compound. Thus, such a novel compound is also included in the present invention. Examples of the aliphatic ether compound in accordance with the present invention include the aliphatic ether compound having the structure represented by any of the chemical formulae (1) to (9).

Such an aliphatic ether compound has high moisture resistance and has physical properties such as low viscosity, low-temperature fluidity, and a high viscosity index, and thus can be suitably used as a base oil of a lubricating oil composition. Especially, in a case where a combination of alkylated phenylnaphthylamine and phosphite ester is used as an antioxidant, a prominent effect of bringing about low evaporability is exerted particularly when an aliphatic ether compound is used among other materials for a base oil.

The aliphatic ether compound in accordance with the present invention has a kinetic viscosity at 40° C. (hereinafter also referred to as "40° C. kinetic viscosity") preferably in a range of 4 cSt to 1000 cSt and more preferably in a range of 4 cSt to 80 cSt. In a case where the 40° C. kinetic viscosity is in the above range, (a) a lubricant composition containing the aliphatic ether compound in accordance with the present invention as a base oil and (b) a bearing oil, a grease, and a freezer oil all of which contain such a lubricant composition can be especially excellent in lubricity and energy-saving.

Further, in a case where the aliphatic ether compound in accordance with the present invention has a viscosity index of preferably not less than 80 and more preferably not less than 110 and has a pour point of preferably not higher than −5° C. and more preferably not higher than −40° C., (a) a lubricant composition containing the aliphatic ether compound in accordance with the present invention as a base oil and (b) a bearing oil, a grease, and a freezer oil all of which contain such a lubricant composition can be especially excellent in low-temperature viscosity property.

The present invention is not limited to the above-described embodiments, but can be altered by a person skilled in the art within the scope of the claims. An embodiment derived from a proper combination of technical means each disclosed in different embodiments is also encompassed in the technical scope of the present invention.

EXAMPLES

The following will specifically describe the present invention with reference to Examples, but the present invention is not limited to the Examples. For convenience, in the drawings, "% by weight" is referred to as "wt %", and only alphanumeric characters given for the lubricant compositions are shown.

[Measurement of Properties of Lubricant Composition]

Properties of the lubricant composition were measured by the following methods.

<Evaporation Loss>

An evaporability test at 180° C. was carried out for evaporation loss measurement. Specifically, 2 g of lubricant composition was put into a cylindrical test container made from stainless steel (SUS 304), 20 mm in internal diameter, and 35 mm in height. The lubricant composition in the container was allowed to stand at 180° C. for a predetermined length of time in a thermostatic chamber equipped with a rotary table. The weight of the resulting lubricant composition was measured. The evaporation loss was obtained by the equation expressed below. Note that a mean of two measurement values was used as a measurement result.

Evaporation loss (% by weight)=(2($g$)−weight($g$) of the lubricant composition having been allowed to stand for a predetermined period of time)× 100/2($g$)

<Decomposition Rate of Base Oil after Elapse of 65 Hours>

Ten grams of sample, 1 g of water, and 4 g of metal powder (88% by weight of copper, 10% by weight of tin, and 2% by weight of zinc) of a copper-based sintered bearing were sealed in a pressure-resistant container made from stainless steel (SUS), and were then stirred while being heated for 65 hours at 160° C. The samples having yet to be tested and having been tested were analyzed by gas chromatography. With the use of a base-oil residual rate, a decomposition rate of the base oil after an elapse of 65 hours was then determined by the following equation:

Decomposition rate (%) of the base oil after the elapse of 65 hours=100−Base-oil residual rate (GC %)

<40° C. Kinetic Viscosity>

Kinetic viscosity at 40° C. was measured with use of a Cannon-Fenske viscometer in accordance with JIS K 2283.

<100° C. Kinetic Viscosity>

Kinetic viscosity at 100° C. was measured with use of a Cannon-Fenske viscometer in accordance with JIS K 2283.

<Viscosity Index>

Viscosity index was calculated in accordance with JIS K 2283.

<Absolute Viscosity>

Absolute viscosity was measured with use of a digital viscometer (DV-II+Pro) manufactured by Brookfield AMETEK, Inc.

<Pour Point>

Pour point was measured in accordance with JIS K 2269.

Synthesis of Base Oil

Production Example 1: Production of Compound 1

Figure 8:
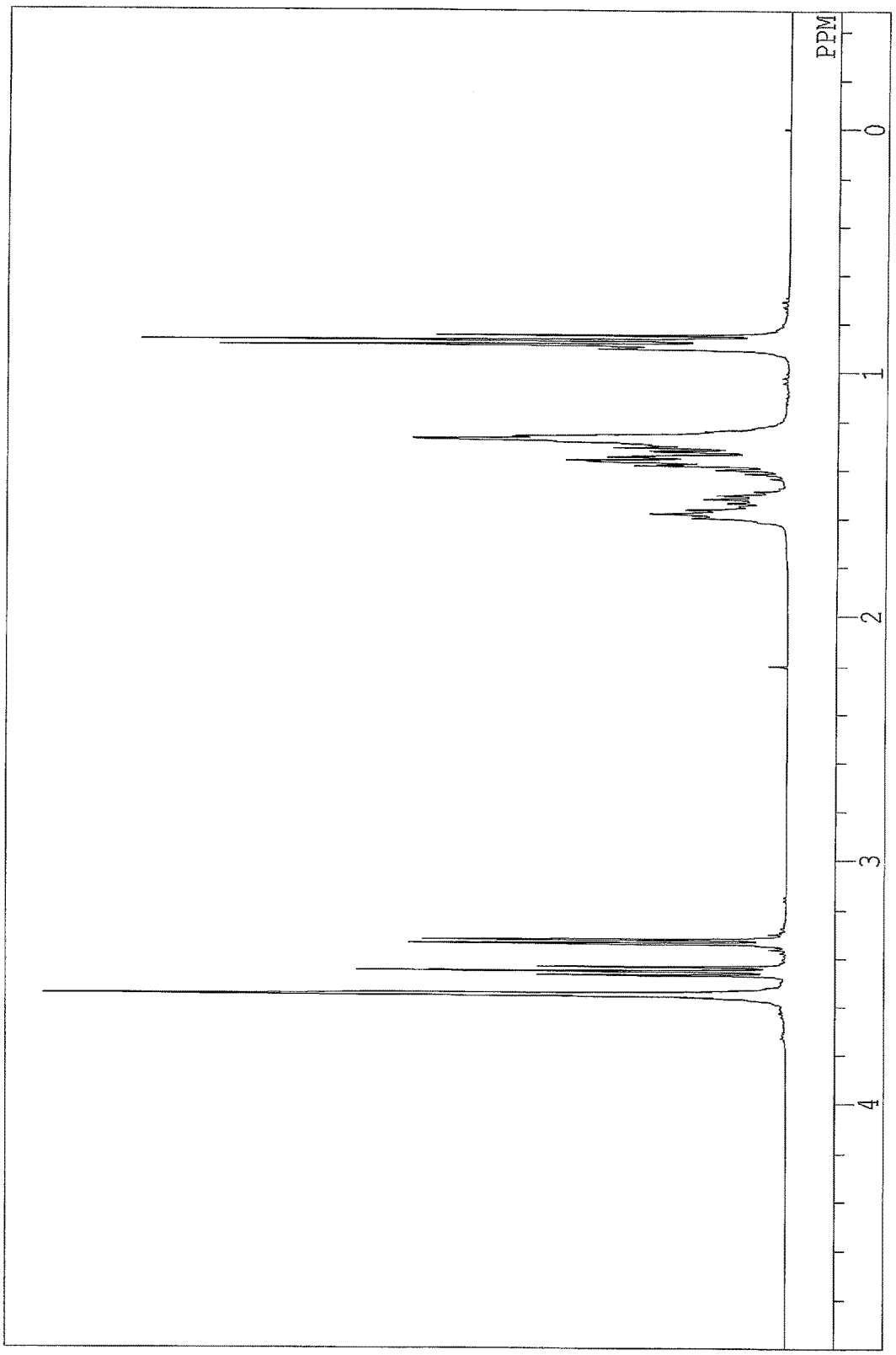
FIG. 8 is a view showing $^1$H-NMR chart of a compound 1 obtained in Production Example 1 of the present invention.

Into a 2-liter glass flask were put 1046 g of 2-ethylhexyloxy ethyl alcohol, 230 g of 1,6-dichlorohexane, and 219 g of potassium hydroxide, and the ingredients were stirred for 1 hour at 180° C. and reacted. Thereafter, the reaction solution was cooled down to room temperature and was then made neutral with a hydrochloric acid added thereto for neutralization of excess alkali. After the reaction solution was washed with 2 liters of water, a separatory funnel was used to separate an organic layer from the reaction solution. The organic layer was then subjected to reduced-pressure distillation to isolate the compound 1 therefrom. FIG. 8 shows $^1$H-NMR chart of the compound 1 thus obtained.

Production Example 2: Production of Compound 2

Into a 10-liter glass flask were put 1310 g of 2-(2-ethylhexyloxy)ethyl alcohol, 3048 g of 1,4-dichlorobutane, and 438 g of potassium hydroxide, and the ingredients were stirred for 16 hours at 90° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate 4-[2-(2-ethylhexyloxy)ethoxy]-butyl chloride therefrom. Subsequently, 2158 g of 2-butyloctanol, 1185 g of 4-[2-(2-ethylhexyloxy)ethoxy]-butyl chloride, and 282 g of potassium hydroxide were put into a 5-liter glass flask, and the ingredients were stirred for 5 hours at 180° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate the compound 2 therefrom.

Production Example 3: Production of Compound 3

Figure 9:
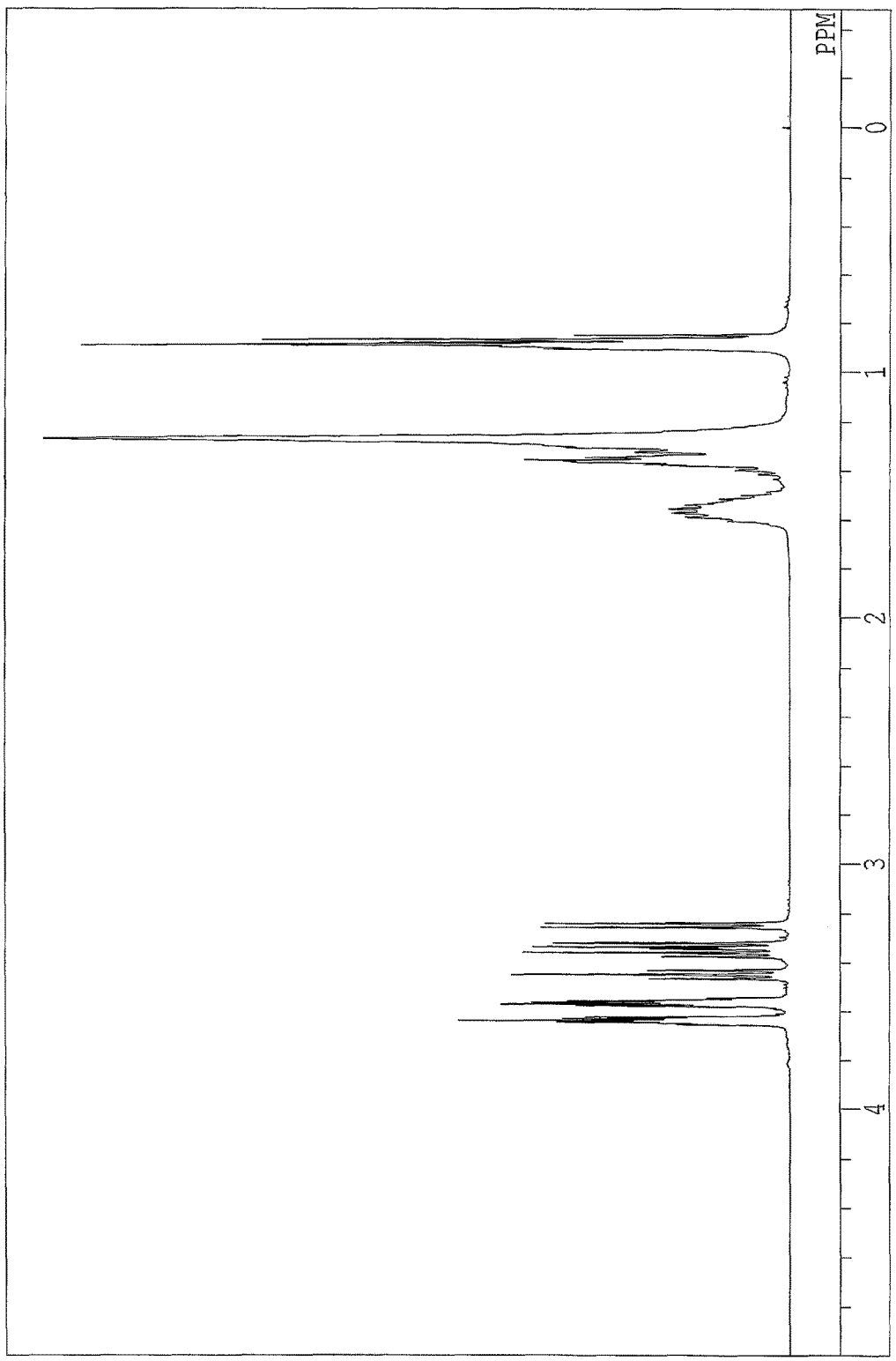
FIG. 9 is a view showing $^1$H-NMR chart of a compound 3 obtained in Production Example 3 of the present invention.

Into a 10-liter glass flask were put 1310 g of 2-(2-ethylhexyloxy)ethyl alcohol, 3673 g of 1,6-dichlorohexane, and 438 g of potassium hydroxide, and the ingredients were stirred for 16 hours at 90° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate 6-[2-(2-ethylhexyloxy)ethoxy]-hexyl chloride therefrom. Subsequently, 2158 g of 2-butyloctanol, 1293 g of 6-[2-(2-ethylhexyloxy)ethoxy]-hexyl chloride, and 282 g of potassium hydroxide were put into a 5-liter glass flask, and the ingredients were stirred for 5 hours at 180° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate the compound 3 therefrom. FIG. 9 shows $^1$H-NMR chart of the compound 3 thus obtained.

Production Example 4: Production of Compound 4

Into a 10-liter glass flask were put 1310 g of 2-(2-ethylhexyloxy)ethyl alcohol, 3673 g of 1,6-dichlorohexane, and 438 g of potassium hydroxide, and the ingredients were stirred for 16 hours at 90° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate 6-[2-(2-ethylhexyloxy)ethoxy]-hexyl chloride therefrom. Subsequently, 1508 g of 1-octanol, 1293 g of 6-[2-(2-ethylhexyloxy)ethoxy]-hexyl chloride, and 282 g of potassium hydroxide were put into a 5-liter glass flask, and the ingredients were stirred for 5 hours at 180° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate the compound 4 therefrom.

Production Example 5: Production of Compound 5

Into a 10-liter glass flask were put 1310 g of 2-(2-ethylhexyloxy)ethyl alcohol, 3673 g of 1,6-dichlorohexane, and 438 g of potassium hydroxide, and the ingredients were stirred for 16 hours at 90° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate 6-[2-(2-ethylhexyloxy)ethoxy]-hexyl chloride therefrom. Subsequently, 1832 g of 1-decanol, 1293 g of 6-[2-(2-ethylhexyloxy)ethoxy]-hexyl chloride, and 282 g of potassium hydroxide were put into a 5-liter glass flask, and the ingredients were stirred for 5 hours at 180° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution.

Figure 10:
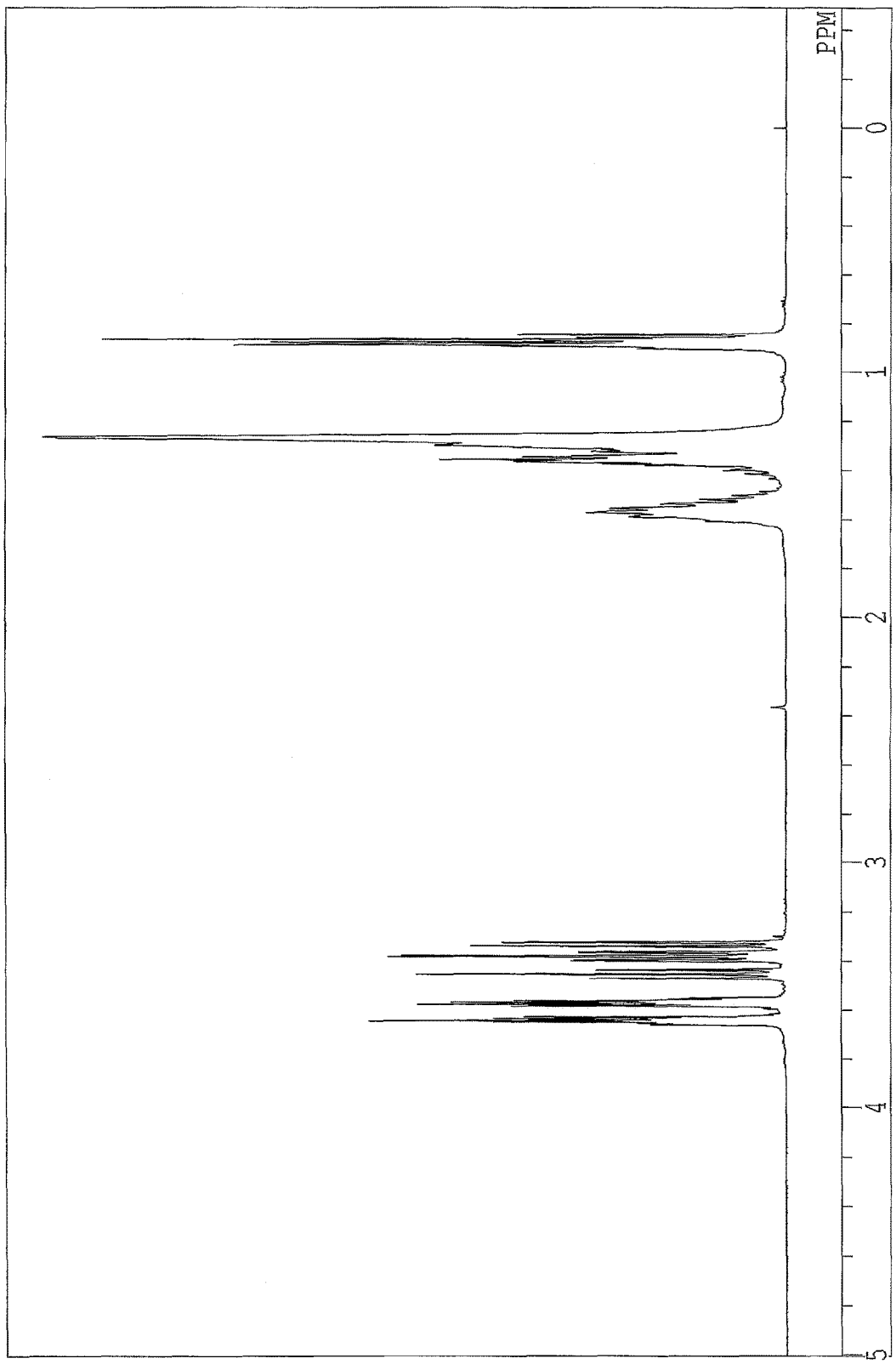
FIG. 10 is a view showing $^1$H-NMR chart of a compound 5 obtained in Production Example 5 of the present invention.

The organic layer was then subjected to reduced-pressure distillation to isolate the compound 5 therefrom. FIG. 10 shows $^1$H-NMR chart of the compound 5 thus obtained.

Production Example 6: Production of Compound 6

Figure 11:
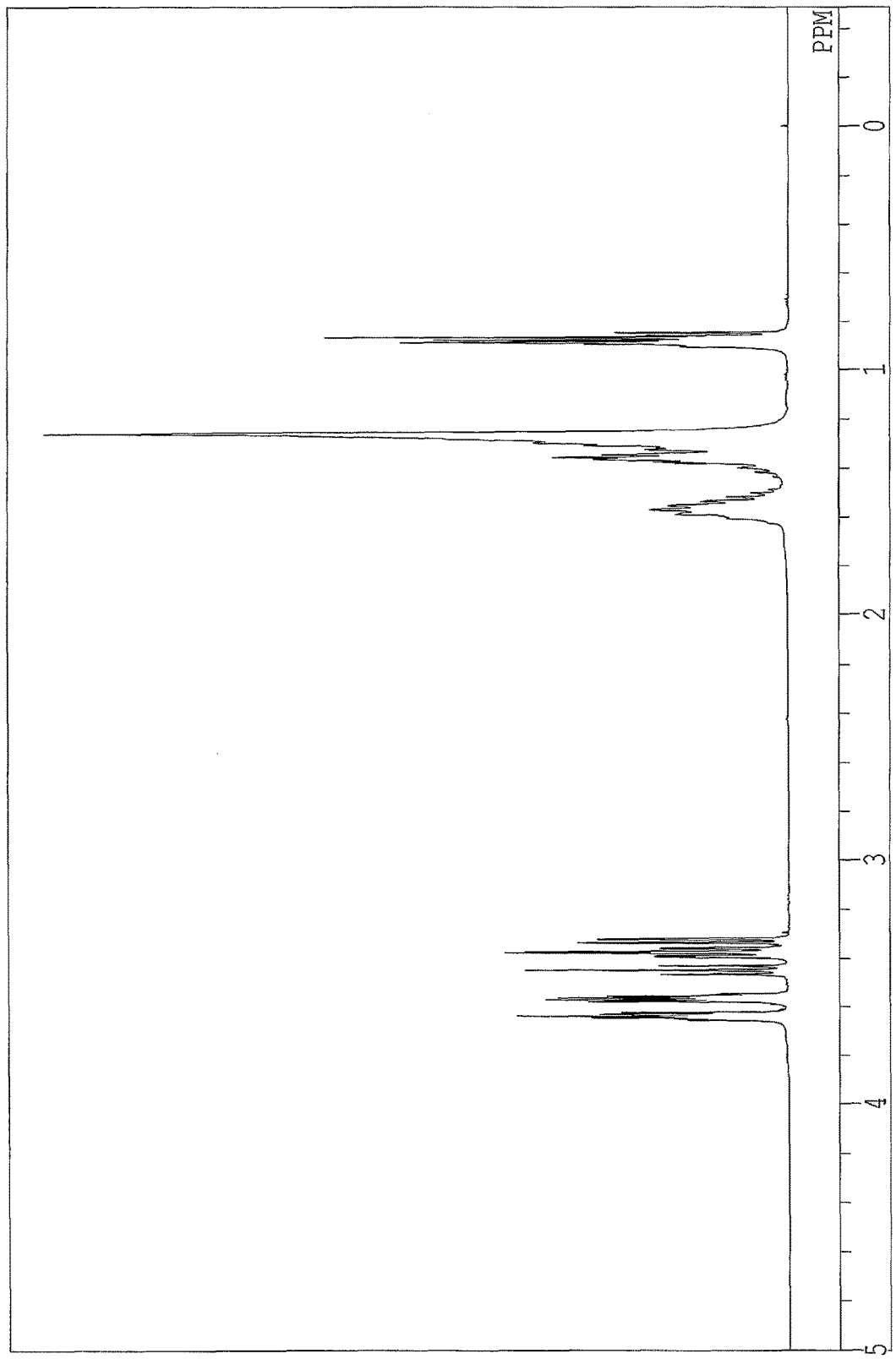
FIG. 11 is a view showing $^1$H-NMR chart of a compound 6 obtained in Production Example 6 of the present invention.

Into a 10-liter glass flask were put 1310 g of 2-(2-ethylhexyloxy)ethyl alcohol, 3673 g of 1,6-dichlorohexane, and 438 g of potassium hydroxide, and the ingredients were stirred for 16 hours at 90° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate 6-[2-(2-ethylhexyloxy)ethoxy]-hexyl chloride therefrom. Subsequently, 2158 g of 1-dodecanol, 1293 g of 6-[2-(2-ethylhexyloxy)ethoxy]-hexyl chloride, and 282 g of potassium hydroxide were put into a 5-liter glass flask, and the ingredients were stirred for 5 hours at 180° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate the compound 6 therefrom. FIG. 11 shows $^1$H-NMR chart of the compound 6 thus obtained.

Production Example 7: Production of Compound 7

Into a 10-liter glass flask were put 1310 g of 2-(2-ethylhexyloxy)ethyl alcohol, 3048 g of 1,4-dichlorobutane, and 438 g of potassium hydroxide, and the ingredients were stirred for 16 hours at 90° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate 4-[2-(2-ethylhexyloxy)ethoxy]-butyl chloride therefrom. Subsequently, 1508 g of 1-octanol, 1185 g of 4-[2-(2-ethylhexyloxy)ethoxy]-butyl chloride, and 282 g of potassium hydroxide were put into a 5-liter glass flask, and the ingredients were stirred for 5 hours at 180° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate compound 7 therefrom.

Production Example 8: Production of Compound 8

Into a 10-liter glass flask were put 1310 g of 2-(2-ethylhexyloxy)ethyl alcohol, 3048 g of 1,4-dichlorobutane, and 438 g of potassium hydroxide, and the ingredients were stirred for 16 hours at 90° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate 4-[2-(2-ethylhexyloxy)ethoxy]-butyl chloride therefrom. Subsequently, 1832 g of 1-decanol, 1185 g of 4-[2-(2-ethylhexyloxy)ethoxy]-butyl chloride, and 282 g of potassium hydroxide were put into a 5-liter glass flask, and the ingredients were stirred for 5 hours at 180° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate the compound 8 therefrom.

Production Example 9: Production of Compound 9

Into a 10-liter glass flask were put 1310 g of 2-(2-ethylhexyloxy)ethyl alcohol, 3048 g of 1,4-dichlorobutane, and 438 g of potassium hydroxide, and the ingredients were stirred for 16 hours at 90° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate 4-[2-(2-ethylhexyloxy)ethoxy]-butyl chloride therefrom. Subsequently, 2158 g of 1-dodecanol, 1185 g of 4-[2-(2-ethylhexyloxy)ethoxy]-butyl chloride, and 282 g of potassium hydroxide were put into a 5-liter glass flask, and the ingredients were stirred for 5 hours at 180° C. and reacted. Thereafter, the reaction solution was cooled down to room temperature and was then made neutral with a hydrochloric acid added thereto for neutralization of excess alkali. After the reaction solution was washed with 3 liters of water, a separatory funnel was used to separate an organic layer from the reaction solution. The organic layer was then subjected to reduced-pressure distillation to isolate the compound 9 therefrom.

Production Example 10: Production of Compound 10

Figure 12:
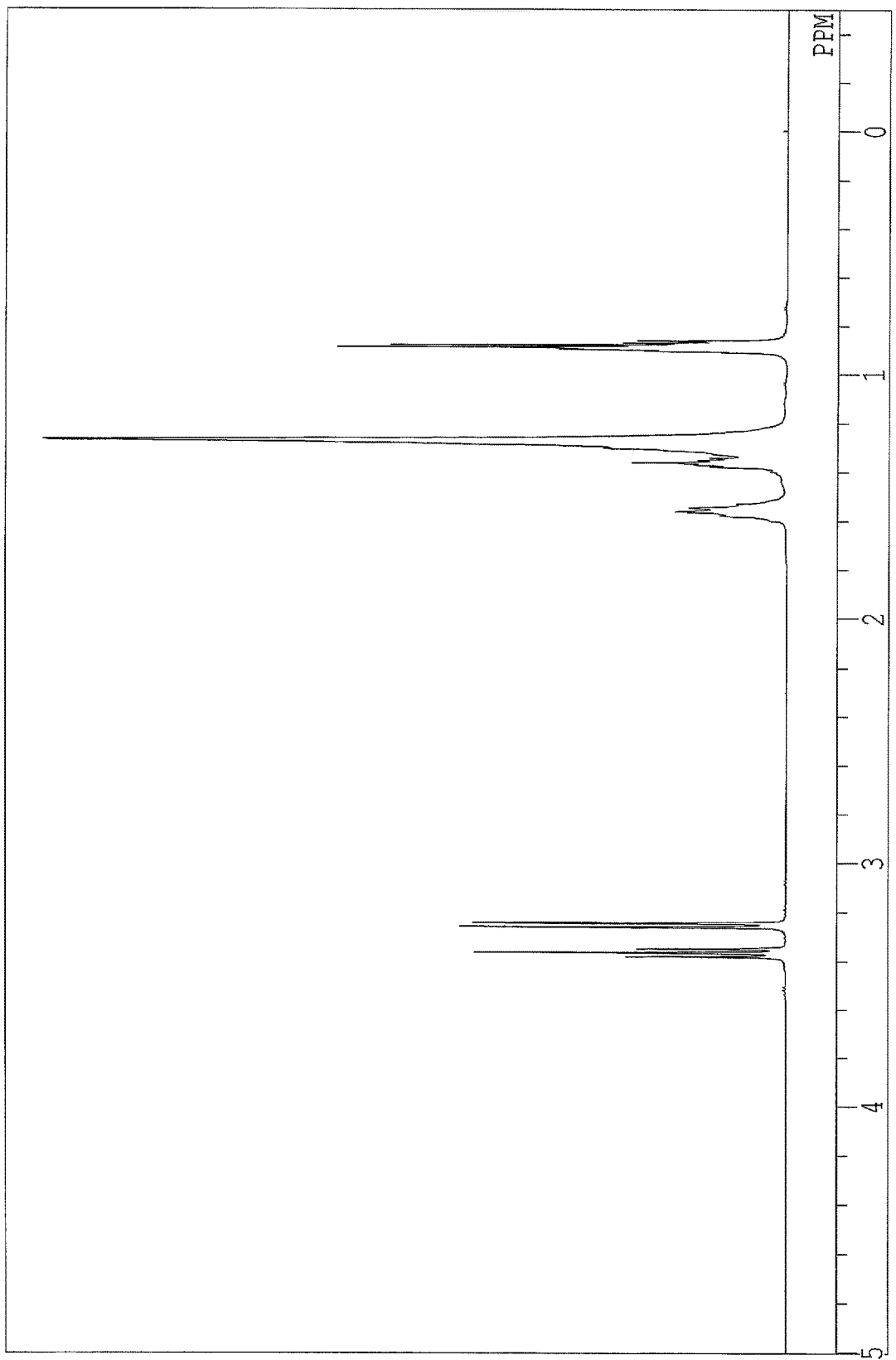
FIG. 12 is a view showing $^1$H-NMR chart of a compound obtained in Production Example 10 of the present invention.

Into a 2-liter glass flask were put 1117 g of 2-butyloctanol, 191 g of 1,4-dichlorobutane, and 219 g of potassium hydroxide, and the ingredients were stirred for 16 hours at 180° C. and reacted. Thereafter, the reaction solution was cooled down to room temperature and was then made neutral with a hydrochloric acid added thereto for neutralization of excess alkali. After the reaction solution was washed with 2 liters of water, a separatory funnel was used to separate an organic layer from the reaction solution. The organic layer was then subjected to reduced-pressure distillation to isolate the compound 10 therefrom. FIG. 12 shows $^1$H-NMR chart of the compound 10 thus obtained.

[Base Oil and Additives]

The base oils obtained in the above Synthesis Examples and the following base oils and additives were used in Examples, Reference Examples, and Comparative Examples below.

<Base Oil>

Dioctyl sebacate (hereinafter also referred to as "DOS")
MORESCO WHITE P-70 (MORESCO Corporation; liquid paraffin)

MORESCO-HILUBE LB-15 (MORESCO Corporation; alkyl diphenyl ether)
UNISTER® H334R (Nichiyu Corporation; triester derived from trimethylolpropane)
ADEKA CARPOL M-60 (ADEKA Corporation; polyalkylene glycol)
MPDC9 (3-methyl-1,5-pentanediol dinonanoate; synthesized by the method described in Japanese Patent No. 4466850)
MPDC11 (3-methyl-1,5-pentanediol diundecanoate; synthesized by the method described in Japanese Patent No. 4466850)
<Alkylated Phenylnaphthylamine-Based Antioxidant>
IRGANOX L06 (BASF Corporation; N-phenyl-1,1,3,3-tetramethylbutylnaphthalene-1-amine (also referred to as "L06" in the Tables))
Naugalube APAN (Chemtura Corporation; N-phenyl-2,4,6,8-tetramethyloctylnaphthalene-1-amine (also referred to as "APAN" in the Tables))
<Diphenylamine-Based Antioxidant>
IRGANOX L57 (BASF Corporation; 2,4,4-trimethylpentyldiphenylamine)
<Phenol-Based Antioxidant>
AO-50F (ADEKA Corporation; n-octadecyl-3-(4'-hydroxy-3'-5'-di-t-butylphenyl)propionate)
<Phosphite Ester-Based Antioxidant>
ADK STAB 522A (ADEKA Corporation; 1,1,3-tris(2-methyl-4-ditridecylphosphite-5-t-butylphenyl)butane)
<Metal Deactivator>
IRGAMET 39 (BASF Corporation; N,N-bis(2-ethylhexyl)-(4 or 5)-methyl-1H-benzotriazole-1-methylamine)
<Corrosion Inhibitor>
IRGACOR L12 (BASF Corporation; a mixture of esters of tetrapropenylsuccinic acid and 1,2-propanediol, mineral oil, and tetrapropenylsuccinic acid)

Reference Examples 1 to 3 and Comparative Examples 1 to 5

The lubricant compositions I to P, which have compositions as shown in Table 1, were prepared with the use of the compound 6 as a base oil. The lubricant compositions I to P were allowed to stand at 180° C. in a thermostatic chamber equipped with a rotary table for varying lengths of time, and evaporation losses thereof were then measured.

Results are shown in FIG. 1. Note that, in FIGS. 1 to 7, a vertical axis indicates evaporation loss (dimensions: % by weight), and a horizontal axis indicates a standing time (in the drawings, represented by "ELAPSED TIME"; dimensions: hours). As shown in FIG. 1, Reference Example 1, which used a combination of alkylated phenylnaphthylamine and phosphite ester as an antioxidant in such a ratio that the alkylated phenylnaphthylamine and the phosphite ester accounted for 95% by weight and 5% by weight, respectively, showed little evaporation loss and showed a large amount of time elapsed before the evaporation loss started increasing with a steep gradient. In Reference Example 2, the alkylated phenylnaphthylamine and the phosphite ester accounted for 90% by weight and 10% by weight, respectively. In Reference Example 3, the alkylated phenylnaphthylamine and the phosphite ester accounted for 85% by weight and 15% by weight, respectively. Reference Examples 2 and 3 showed less evaporation losses and showed larger amounts of time elapsed before the evaporation loss started increasing with a steep gradient. This is considered to be caused because the combined use of alkylated phenylnaphthylamine and phosphite ester as an antioxidant in the above-described ratios further increases effectiveness for antioxidation and further prolongs the duration of effectiveness for antioxidation.

On the other hand, Comparative Example 1, which used the alkylated phenylnaphthylamine alone as an antioxidant without using phosphite ester, showed an evaporation loss that largely increased at an earlier point in time, as compared to the cases in which the alkylated phenylnaphthylamine and the phosphite ester were used in combination as an antioxidant.

Further, Comparative Example 4, which used the phosphite ester alone as an antioxidant without using alkylated phenylnaphthylamine, showed an evaporation loss that started increasing at an earlier point in time, as compared to the cases in which alkylated phenylnaphthylamine and phosphite ester were used in combination as an antioxidant.

Still further, Comparative Example 2, in which the alkylated phenylnaphthylamine and the phosphite ester accounted for 97% by weight and 3% by weight, respectively, and Comparative Example 3, in which the alkylated phenylnaphthylamine and the phosphite ester accounted for 80% by weight and 20% by weight, respectively, showed significantly greater evaporation losses, as compared to Reference Examples 1 to 3, in which the alkylated phenylnaphthylamine and the phosphite ester accounted for 85% to 95% by weight and 15% to 5% by weight, respectively.

Yet further, Comparative Example 5, which used the phenol-based antioxidant without using the phosphite ester and the alkylated phenylnaphthylamine as an antioxidant, showed a greater evaporation loss than the cases in which the alkylated phenylnaphthylamine and the phosphite ester were used in combination as an antioxidant.

Examples 1 and 2 and Comparative Examples 6 to 10

The lubricant compositions Q to W, which have compositions as shown in Table 2, were prepared with the use of

TABLE 1

| | | | Comparative Example 1 | Comparative Example 2 | Reference Example 1 | Reference Example 2 | Reference Example 3 | Comparative Example 3 | Comparative Example 4 | (wt %) Comparative Example 5 |
|---|---|---|---|---|---|---|---|---|---|---|
| Lubricant composition | | | I | J | K | L | M | N | O | P |
| Base oil (compound 6) | | | 98.00 | 98.00 | 98.00 | 98.00 | 98.00 | 98.00 | 98.00 | 97.00 |
| Antioxidant | Alkylated phenylnaphthylamine | L06 | 2.00 | 1.94 | 1.90 | 1.80 | 1.70 | 1.60 | 0 | 0 |
| | Phenol | AO-50F | 0 | 0 | 0 | 0 | 0 | 0 | 0 | 3 |
| | Phosphite ester | 522A | 0 | 0.06 | 0.10 | 0.20 | 0.30 | 0.40 | 2.00 | 0 |
| Ratio of phosphite ester in antioxidant | | | 0 | 3 | 5 | 10 | 15 | 20 | 100 | 0 | the compound 6 as a base oil. The lubricant compositions Q to W were allowed to stand at 180° C. in a thermostatic chamber equipped with a rotary table for varying lengths of time, and evaporation losses thereof were then measured.

In Comparative Examples 8 and 9, a ratio between the alkylated phenylnaphthylamine and the phosphite ester was as follows: In Comparative Example 8, the alkylated phenylnaphthylamine and the phosphite ester accounted for

TABLE 2

| | | | Comparative Example 6 | Comparative Example 7 | Example 1 | Example 2 | Comparative Example 8 | Comparative Example 9 | (wt %) Comparative Example 10 |
|---|---|---|---|---|---|---|---|---|---|
| Lubricant composition | | | Q | R | S | T | U | V | W |
| Base oil (compound 6) | | | 97.00 | 96.50 | 96.80 | 96.50 | 96.30 | 96.00 | 96.50 |
| Antioxidant | Alkylated phenylnaphthylamine | L06 | 3.00 | 3.50 | 3.00 | 3.00 | 3.00 | 3.00 | 0 |
| | Phenol | AO-50F | 0 | 0 | 0 | 0 | 0 | 0 | 3.00 |
| | Phosphite ester | 522A | 0 | 0 | 0.20 | 0.50 | 0.70 | 1.00 | 0.50 |
| Ratio of phosphite ester in antioxidant | | | 0 | 0 | 6.25 | 14.28 | 18.92 | 25.00 | 14.28 |
| Low evaporability rating | | | C | C | A | A | B | B | C |

Figure 2:
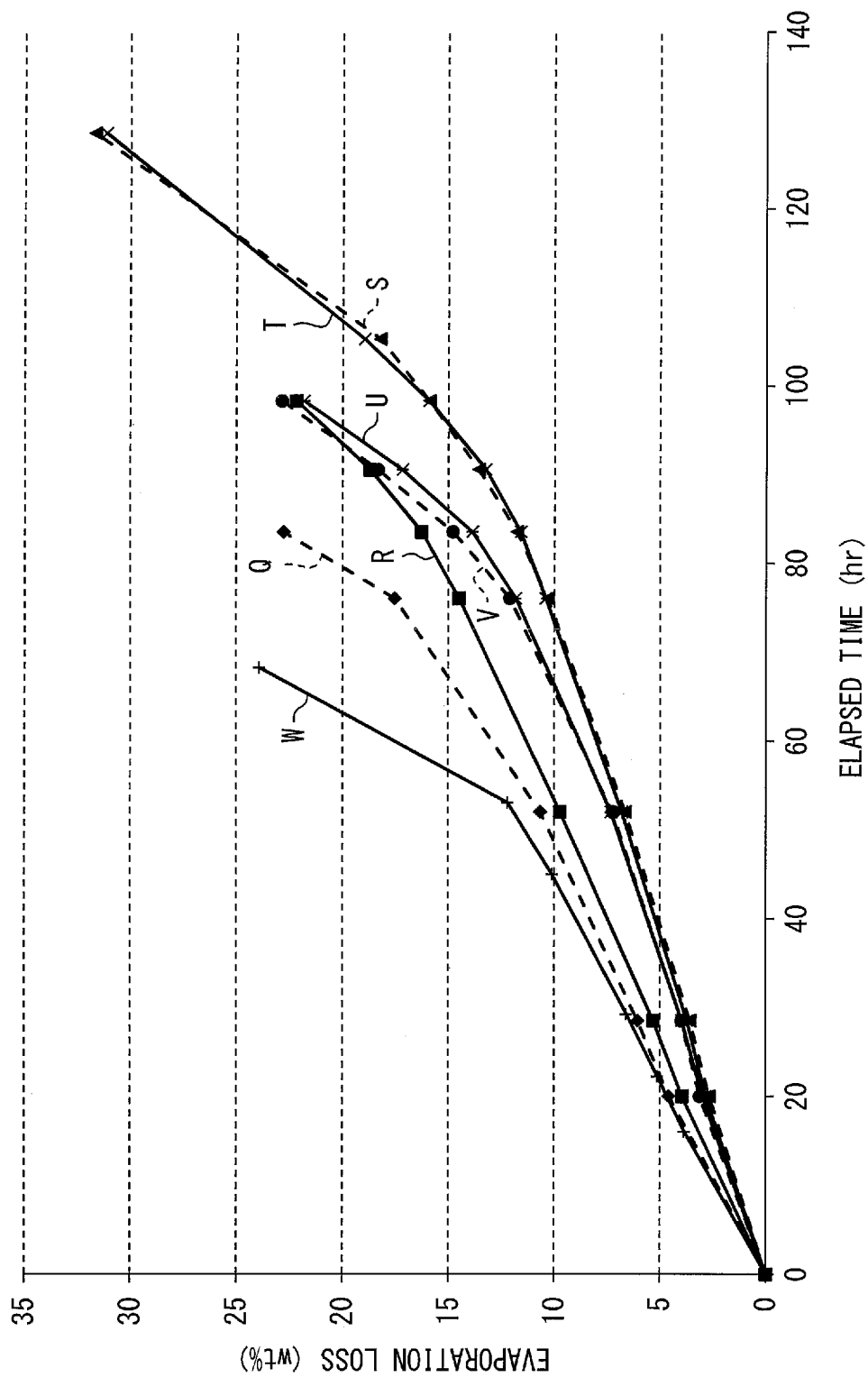
FIG. 2 is a graph showing results of measurement of evaporation losses of lubricant compositions prepared in Examples 1 and 2 of the present invention and in Comparative Examples 6 to 10.

Results are shown in FIG. 2. Table 2 shows low evaporability ratings. In Table 2, "A" indicates excellent low evaporability, "B" indicates insufficient low evaporability, and "C" indicates poor low evaporability.

Comparative Example 6 used the alkylated phenylnaphthylamine alone as an antioxidant in an amount of 3.00% by weight relative to the total amount of the lubricating oil composition. Meanwhile, Comparative Example 7 used the alkylated phenylnaphthylamine alone as an antioxidant in an amount larger by 0.50% by weight than Comparative Example 6, i.e., in an amount of 3.50% by weight relative to the total amount of lubricating oil composition.

On the other hand, unlike Comparative Example 7, instead of using the alkylated phenylnaphthylamine alone as an antioxidant in an amount larger by 0.50% by weight than Comparative Example 6, Example 2 additionally used the phosphite ester in an amount of 0.50% by weight. As can be seen in FIG. 2, the result was such that Example 2, which used the phosphite ester in the amount of 0.50% by weight, showed significantly less evaporation loss than Comparative Example 7, which used the alkylated phenylnaphthylamine in an amount larger by 0.50% by weight than Comparative Example 6, which contained the alkylated phenylnaphthylamine in an amount of 3.00% by weight relative to the total amount of the lubricating oil composition. Such a result demonstrates that the combined use of alkylated phenylnaphthylamine and phosphite ester achieves a synergistic effect, which surpasses an effect yielded by an increase in total amount of antioxidant, of promoting low evaporability. In addition, it was shown that Example 1, which contained the alkylated phenylnaphthylamine in an amount of 3.00% by weight relative to the total amount of the lubricating oil composition like Comparative Example 6, but contained the phosphite ester in an amount as low as 0.20% by weight, achieves a prominent effect of promoting low evaporability.

As can also be seen in FIG. 2, Comparative Example 10, which used an antioxidant made from the (a) phenol-based antioxidant and the (b) phosphite ester in a ratio that is the same as the ratio between the alkylated phenylnaphthylamine and the phosphite ester in Example 2 and had the same antioxidant content as that in Example 2 relative to the base oil, showed an evaporation loss that was greater than the evaporation loss of Example 2 and that started increasing with a steep gradient at an earlier point in time than the evaporation loss of Example 2. Such a result demonstrates that the combined use of phenol-based antioxidant and phosphite ester cannot achieve low evaporability which is obtained by the combined use of alkylated phenylnaphthylamine and phosphite ester.

81.08% by weight and 18.92% by weight, respectively. In Comparative Example 9, the alkylated phenylnaphthylamine and the phosphite ester accounted for 75% by weight and 25% by weight, respectively. Comparative Examples 8 and 9 showed greater evaporation losses, as compared to Examples 1 and 2, in which the alkylated phenylnaphthylamine and the phosphite ester accounted for 85% to 95% by weight and 15% to 5% by weight, respectively.

Reference Examples 4 and 5 and Comparative Examples 11 to 14

The lubricant compositions 1 to 12, which have compositions as shown in Table 3, were prepared. As shown in Table 3, lubricant compositions that each used the alkylated phenylnaphthylamine alone as an antioxidant together with various base oils (In Table 3, referred to as "SINGLE") and lubricant compositions that each used the antioxidant made from a combination of alkylated phenylnaphthylamine and phosphite ester together with various base oils (In Table 3, referred to as "COMBINED") were prepared. These lubricant compositions were allowed to stand at 180° C. in a thermostatic chamber equipped with a rotary table for 16.5 hours, and a rate of reduction of evaporation loss that occurred with the combined use of alkylated phenylnaphthylamine and phosphite ester was then calculated.

Note that the rate of reduction of evaporation loss that occurred with the combined use of alkylated phenylnaphthylamine and phosphite ester (hereinafter also referred to as "rate of reduction of evaporation loss that occurred with the combined use") was calculated by the following equation:

Rate (%) of reduction of evaporation loss that occurred with the combined use=100−100×(evaporation loss of the lubricating oil composition containing the antioxidant made from a combination of alkylated phenylnaphthylamine and phosphite ester after the elapse of 16.5 hours/evaporation loss of the lubricating oil composition containing the alkylated phenylnaphthylamine alone as an antioxidant after the elapse of 16.5 hours)

TABLE 3

|  |  | | Comparative Example 11 | | Comparative Example 12 | | Comparative Example 13 | |
|---|---|---|---|---|---|---|---|---|
| Types of base oil | | | DOS | | P-70 | | LB-15 | |
| Lubricant composition | | | 1 | 2 | 3 | 4 | 5 | 6 |
| | | | Single | Combined | Single | Combined | Single | Combined |
| Base oil (wt %) | | | 99.00 | 99.00 | 99.00 | 99.00 | 99.00 | 99.00 |
| Antioxidant (wt %) | Alkylated phenylnaphthylamine | APAN | 1.00 | 0.90 | 1.00 | 0.90 | 1.00 | 0.90 |
| | Phosphite ester | 522A | 0 | 0.10 | 0 | 0.10 | 0 | 0.10 |
| | | | Comparative Example 14 | | Reference Example 4 | | Reference Example 5 | |
| Types of base oil | | | HS34R | | Compound 6 | | M-60 | |
| Lubricant composition | | | 7 | 8 | 9 | 10 | 11 | 12 |
| | | | Single | Combined | Single | Combined | Single | Combined |
| Base oil (wt %) | | | 99.00 | 99.00 | 99.00 | 99.00 | 99.00 | 99.00 |
| Antioxidant (wt %) | Alkylated phenylnaphthylamine | APAN | 1.00 | 0.90 | 1.00 | 0.90 | 1.00 | 0.90 |
| | Phosphite ester | 522A | 0 | 0.10 | 0 | 0.10 | 0 | 0.10 |

TABLE 4

|  | Comparative Example 11 | | Comparative Example 12 | | Comparative Example 13 | | Comparative Example 14 | | Reference Example 4 | | Reference Example 5 | |
|---|---|---|---|---|---|---|---|---|---|---|---|---|
| Types of base oil | DOS | | P-70 | | LB-15 | | HS34R | | Compound 6 | | M-60 | |
| Lubricant composition | 1 | 2 | 3 | 4 | 5 | 6 | 7 | 8 | 9 | 10 | 11 | 12 |
| Evaporation loss after elapse of 16.5 hours (wt %) | Single 7.11 | Combined 7.01 | Single 63.02 | Combined 60.77 | Single 19.55 | Combined 19.37 | Single 2.19 | Combined 2.09 | Single 14.01 | Combined 3.34 | Single 35.08 | Combined 16.32 |
| Rate of reduction of evaporation loss (%) | 1.5 | | 3.6 | | 1.0 | | 4.7 | | 76 | | 54 | |

Results are shown in Table 4. In Reference Example 4, which used the aliphatic ether compound (compound 6) represented by the above-described chemical formula (6) as a base oil, the rate (%) of reduction of evaporation loss that occurred with the combined use was 76%. In Reference Example 5, which used polyalkylene glycol that is an aliphatic polyether compound as a base oil, the rate (%) of reduction of evaporation loss that occurred with the combined use was 54%.

On the other hand, in Comparative Example 11, which used dioctyl sebacate that is a diester compound as a base oil, the rate (%) of reduction of evaporation loss that occurred with the combined use was 1.5%. In Comparative Example 12, which used liquid paraffin as a base oil, the rate (%) of reduction of evaporation loss that occurred with the combined use was 3.6%. In Comparative Example 13, which used alkyl diphenyl ether that is an aromatic ether compound as a base oil, the rate (%) of reduction of evaporation loss that occurred with the combined use was 1.0%. In Comparative Example 14, which used hindered ester that is a triester compound as a base oil, the rate (%) of reduction of evaporation loss that occurred with the combined use was 4.7%.

The results obtained in Reference Examples 4 and 5 and Comparative Examples 11 to 14 demonstrate that a high degree of effect produced by the combined use of alkylated phenylnaphthylamine and phosphite ester is an effect exerted particularly when an aliphatic ether compound is used among other materials for a base oil.

Examples 3 to 14 and Comparative Examples 15 and 16

The lubricant compositions L, M, and 13 to 24, which have compositions as shown in Table 5, were prepared with the use of the compound 6 as a base oil. The lubricant compositions L, M, and 13 to 24 were allowed to stand at 180° C. in a thermostatic chamber equipped with a rotary table for varying lengths of time, and evaporation losses thereof were then measured.

TABLE 5

(wt %)

|  | Comparative Example 15 | Comparative Example 16 | Example 3 | Example 4 | Example 5 | Example 6 | Example 7 | Example 8 |
|---|---|---|---|---|---|---|---|---|
| Total amount of antioxidant | 2 | | 4 | | 6 | | 8 | |
| Lubricant composition | L | M | 13 | 14 | 15 | 16 | 17 | 18 |
| Ratio of phosphite ester in antioxidant | 10% | 15% | 10% | 15% | 10% | 15% | 10% | 15% |
| Base oil (compound 6) | 98 | 98 | 96 | 96 | 94 | 94 | 92 | 92 |

TABLE 5-continued

| Antioxidant | Alkylated phenylnaphthylamine | L06 | 1.80 | 1.70 | 3.60 | 3.40 | 5.40 | 5.10 | 7.20 | 6.80 |
|---|---|---|---|---|---|---|---|---|---|---|
| | Phosphite ester | 522A | 0.20 | 0.30 | 0.40 | 0.60 | 0.60 | 0.90 | 0.80 | 1.20 |

| | | | Example 9 | Example 10 | Example 11 | Example 12 | Example 13 | Example 14 (wt %) |
|---|---|---|---|---|---|---|---|---|
| Total amount of antioxidant | | | 4 | | 6 | | 8 | |
| Lubricant composition | | | 19 | 20 | 21 | 22 | 23 | 24 |
| Ratio of phosphite ester in antioxidant | | | 10% | 15% | 10% | 15% | 10% | 15% |
| Base oil (compound 6) | | | 96 | 96 | 94 | 94 | 92 | 92 |
| Antioxidant | Alkylated phenylnaphthylamine | APAN | 3.60 | 3.40 | 5.40 | 5.10 | 7.20 | 6.80 |
| | Phosphite ester | 522A | 0.40 | 0.60 | 0.60 | 0.90 | 0.80 | 1.20 |

Figure 3:
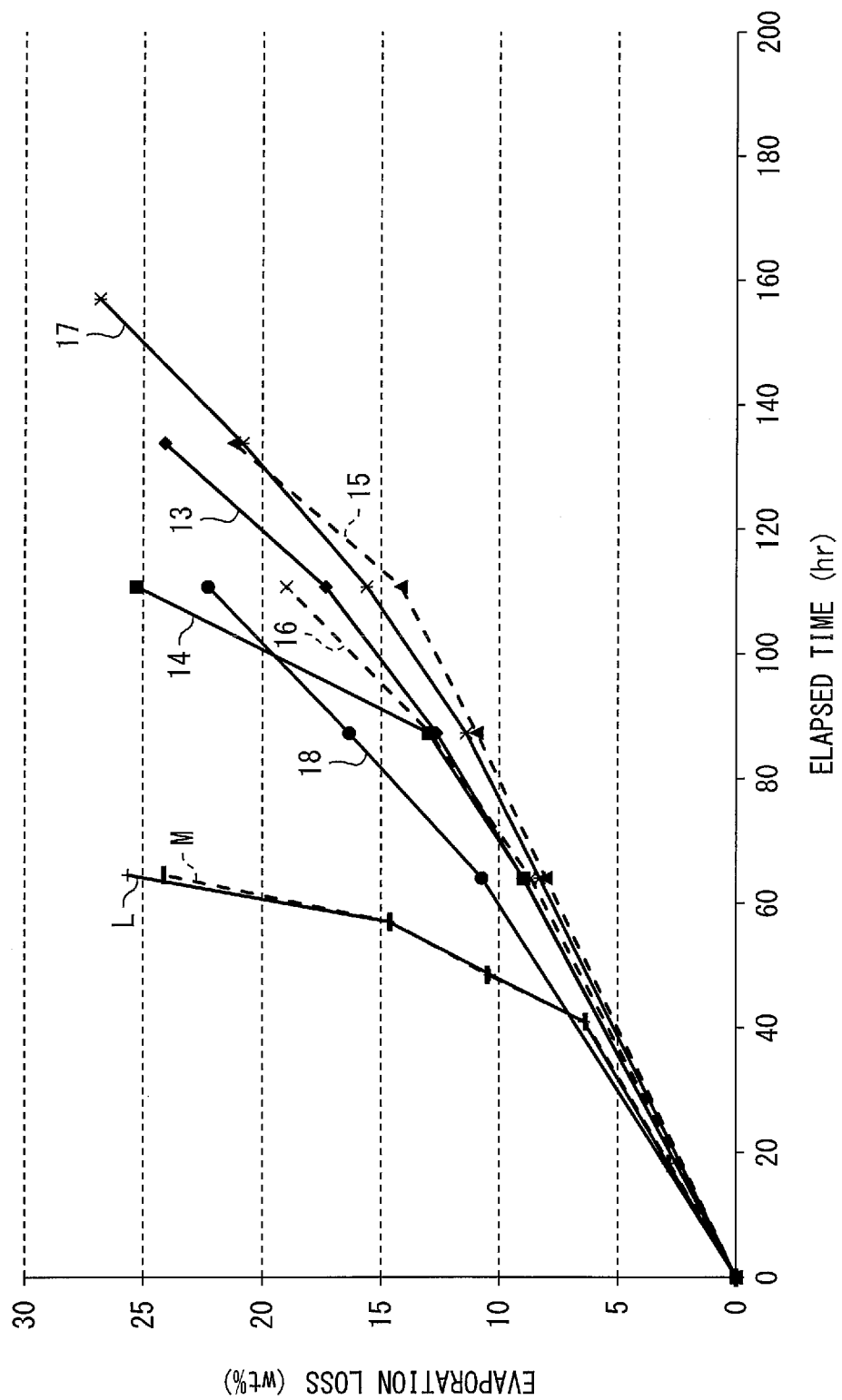
FIG. 3 is a graph showing results of measurement of evaporation losses of lubricant compositions prepared in Examples 3 to 8 of the present invention and in Comparative Examples 15 and 16.
Figure 4:
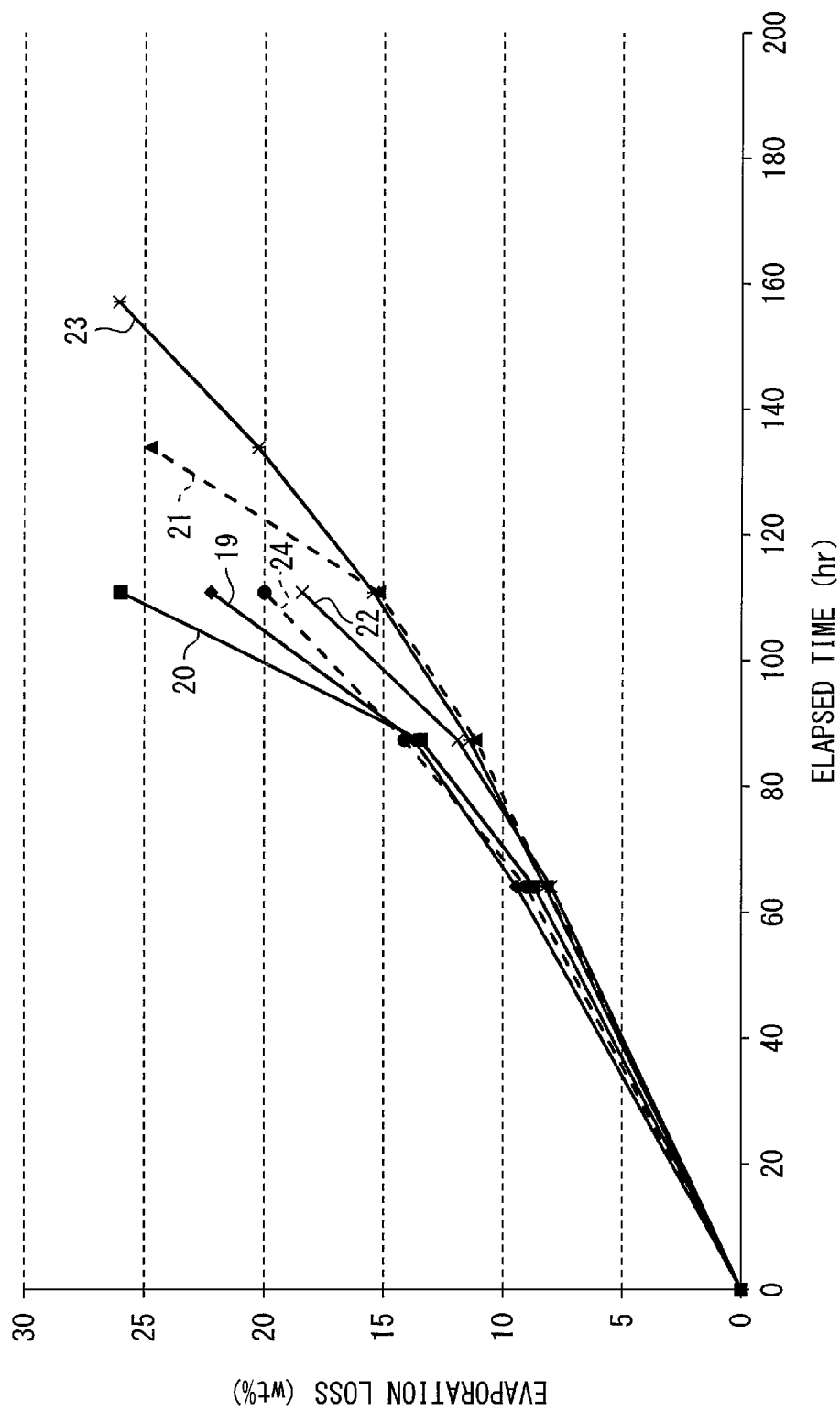
FIG. 4 is a graph showing results of measurement of evaporation losses of lubricant compositions prepared in Examples 9 to 14 of the present invention.

Results are shown in FIGS. 3 and 4. As shown in FIGS. 3 and 4, Examples 3, 4, 9, and 10, in which a sum of individual amounts of the alkylated phenylnaphthylamine and the phosphite ester, both of which were contained in the lubricating oil composition, accounted for 4% by weight of the total amount of the lubricating oil composition, Examples 5, 6, 11, and 12, in which a sum of individual amounts of the alkylated phenylnaphthylamine and the phosphite ester, both of which were contained in the lubricating oil composition, accounted for 6% by weight of the total amount of the lubricating oil composition, and Examples 7, 8, 13, and 14, in which a sum of individual amounts of the alkylated phenylnaphthylamine and the phosphite ester, both of which were contained in the lubricating oil composition, accounted for 8% by weight of the total amount of the lubricating oil composition, showed little evaporation losses and large amounts of time elapsed before the evaporation loss started increasing with a steep gradient.

On the other hand, Comparative Examples 15 and 16, in which individual lubricating oil compositions were prepared as in Examples 3 to 8 except that a sum of individual amounts of the alkylated phenylnaphthylamine and the phosphite ester, both of which were contained in the lubricating oil composition, accounted for 2% by weight of the total amount of the lubricating oil composition, and evaporation losses thereof were measured, showed evaporation losses that were significantly greater than the evaporation losses of Examples 3 to 8 and that started increasing with a steep gradient at an earlier point in time than the evaporation losses of Examples 3 to 8.

Examples 15 to 17 and Comparative Examples 17 to 21

The lubricant compositions A to H, which have compositions as shown in Table 6, were prepared with the use of the compound 5 as a base oil. The lubricant compositions A to H were allowed to stand at 180° C. in a thermostatic chamber equipped with a rotary table for varying lengths of time, and evaporation losses thereof were then measured.

TABLE 6

| | | Comparative Example 17 | Comparative Example 18 | Comparative Example 19 | Comparative Example 20 | Comparative Example 21 | Example 15 | Example 16 | Example 17 (wt %) |
|---|---|---|---|---|---|---|---|---|---|
| Lubricant composition | | A | B | C | D | E | F | G | H |
| Base oil (compound 5) | | 94 | 94 | 94 | 94 | 94 | 94 | 94 | 94 |
| Antioxidant | IRGANOX L57 | 5.5 | 4.5 | 4 | 3.5 | 3 | 2 | 1.5 | 0 |
| | IRGANOX L06 | 0 | 1 | 1.5 | 2 | 2.5 | 3.5 | 4 | 5.5 |
| | 522A | 0.5 | 0.5 | 0.5 | 0.5 | 0.5 | 0.5 | 0.5 | 0.5 |

→ Improved (evaporation amount reduced)

Figure 5:
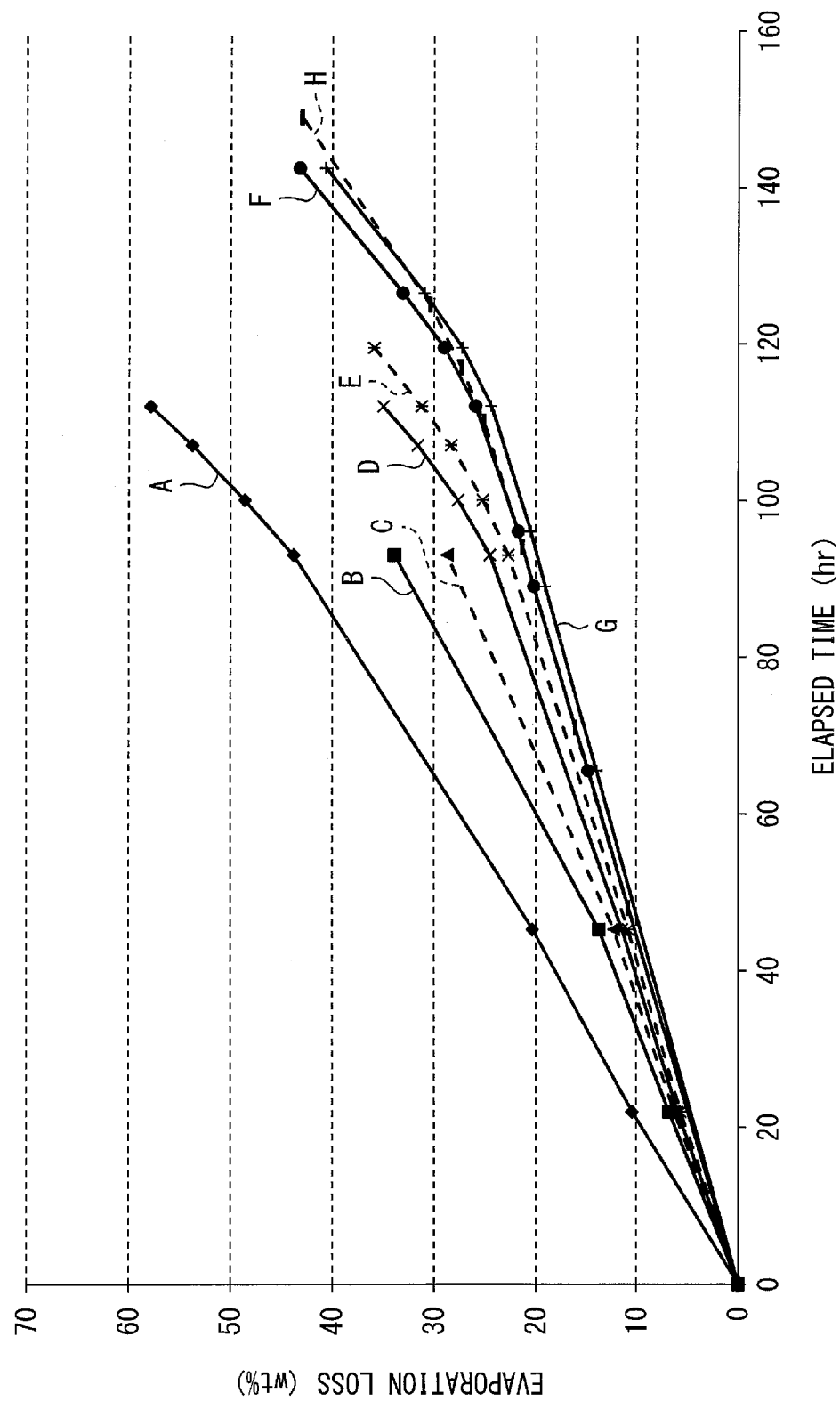
FIG. 5 is a graph showing results of measurement of evaporation losses of lubricant compositions prepared in Examples 15 to 17 of the present invention and in Comparative Examples 17 to 21.

Results are shown in FIG. 5. As shown in Table 6, Comparative Examples 17 to 21 and Examples 15 to 17 used the aliphatic ether compound as a base oil and used, as an antioxidant, a combination of (i) the alkylated phenylnaphthylamine-based antioxidant and/or alkylated diphenylamine-based antioxidant and (ii) the phosphite ester-based antioxidant. In Comparative Examples 17 to 21 and Examples 15 to 17, the amount(s) of the alkylated phenylnaphthylamine-based antioxidant used and/or the alkylated diphenylamine-based antioxidant used was/were fixed at 5.5% by weight of the total amount of the lubricant composition, and the amount of the phosphite ester-based antioxidant used was fixed at 0.5% by weight of the total amount of the lubricant composition, but a ratio between the alkylated phenylnaphthylamine-based antioxidant and the alkylated diphenylamine-based antioxidant was varied.

As shown in FIG. 5, Comparative Example 17, in which the amount of alkylated phenylnaphthylamine-based antioxidant used was 0% by weight, and the amount of alkylated diphenylamine-based antioxidant used was 5.5% by weight, showed an evaporation loss that was greater than evaporation losses of Examples 15 to 17 and Comparative Examples 18 to 21 and that started increasing with a steep gradient at an earlier point in time than evaporation losses of Examples 15 to 17 and Comparative Examples 18 to 21. In Comparative Example 18, Comparative Example 19, Comparative Example 20, Comparative Example 21, Example 15, and Example 16, evaporation losses decreased in this order, and started increasing at later points in time in this order. Example 17, in which the amount of alkylated phenylnaphthylamine-based antioxidant used was 5.5% by weight and the amount of alkylated diphenylamine-based antioxidant used was 0% by weight, showed an evaporation loss that was the lowest and that increased at a late point in time.

Such a result demonstrates that the combination of alkylated diphenylamine-based antioxidant and phosphite ester-based antioxidant cannot achieve the effect, which is achieved by the present invention, of attaining a small amount of evaporation. On the other hand, the combined use of alkylated phenylnaphthylamine and phosphite ester as an antioxidant was found to attain a prominent effect of reducing the amount of evaporation.

Examples 18, 19, and 23 to 26

Lubricant compositions 25, 26 and 33 to 36, which have compositions as shown in Table 7, were prepared. The lubricant compositions 25, 26 and 33 to 36 were allowed to stand at 180° C. in a thermostatic chamber equipped with a rotary table for varying lengths of time, and evaporation losses thereof were then measured. Further, 40° C. kinetic viscosities and 100° C. kinetic viscosities of the lubricant compositions were measured, and viscosity indices were calculated.

TABLE 7

|  |  | Example 18 | Example 19 | Example 23 | Example 24 | Example 25 | (wt %)<br>Example 26 |
|---|---|---|---|---|---|---|---|
| Lubricant composition |  | 25 | 26 | 33 | 34 | 35 | 36 |
| Base oil |  | Compound 6 | Compound 6 | Compound 1 | Compound 1 | Compound 1 | Compound 1 |
|  |  | 93.9 | 95.9 | 95.9 | 95.9 | 95.9 | 96.9 |
| Antioxidant | APAN | 5.4 | 1.8 | 3.6 | 0 | 1.8 | 1.35 |
|  | L 06 | 0 | 1.8 | 0 | 3.6 | 1.8 | 1.35 |
|  | 522A | 0.6 | 0.4 | 0.4 | 0.4 | 0.4 | 0.3 |
| Metal deactivator | IRGAMET 39 | 0.05 | 0.05 | 0.05 | 0.05 | 0.05 | 0.05 |
| Corrosion inhibitor | IRGACOR L12 | 0.05 | 0.05 | 0.05 | 0.05 | 0.05 | 0.05 |
| 40° C. kinetic viscosity |  | 14.07 | 13.41 | 8.86 | 8.90 | 8.79 | 8.64 |
| 100° C. kinetic viscosity |  | 3.82 | 3.73 | 2.66 | 2.70 | 2.66 | 2.64 |
| Viscosity index |  | 176 | 181 | 147 | 153 | 151 | 151 |
| Total amount of antioxidant |  | 6 | 4 | 4 | 4 | 4 | 3 |

Figure 6:
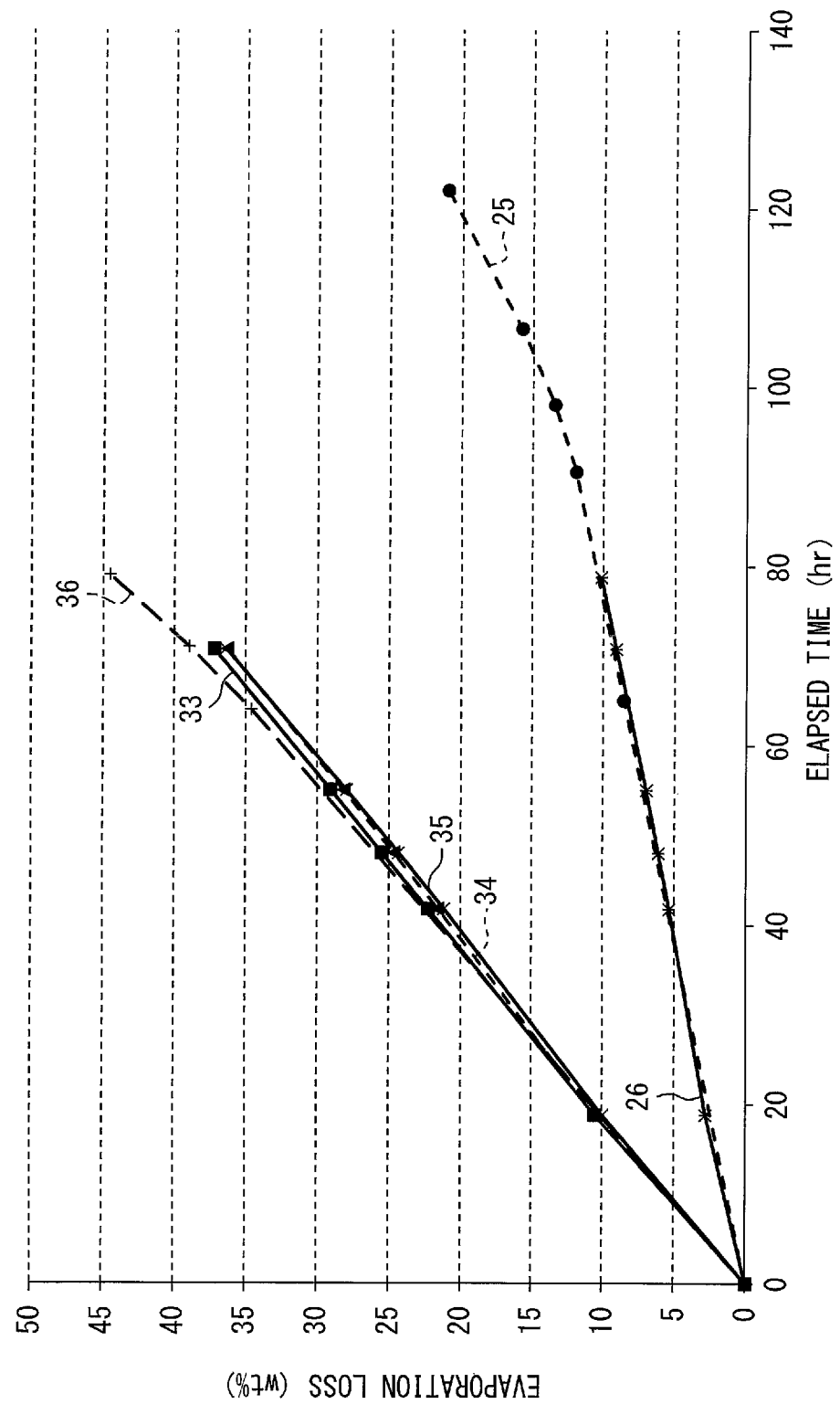
FIG. 6 is a graph showing results of measurement of evaporation losses of lubricant compositions prepared in Examples 18 and 19 of the present invention.

Results are shown in Table 7 and FIG. 6. As shown in Table 7, 40° C. kinetic viscosities, 100° C. kinetic viscosities, and viscosity indices of the obtained lubricant compositions were equal to or more excellent than those of the existing oils in the art. The obtained lubricant compositions were also confirmed to show low evaporability that is equal to or higher in degree than those of the existing oils in the art.

Examples 20 to 22 and Comparative Examples 22 to 24

Lubricant compositions 27 to 32, which have compositions as shown in Tables 8 and 9, were prepared. The lubricant compositions 27 to 32 were allowed to stand at 180° C. in a thermostatic chamber equipped with a rotary table for varying lengths of time, and evaporation losses thereof were then measured. The compositions shown in Table 8 are compositions of the existing lubricating oil compositions in the art. For the obtained lubricating oil composition, the decomposition rate of the base oil after the elapse of 65 hours was measured. Further, for the lubricant composition 25 obtained in Example 18 and the lubricant composition 34 obtained in Example 24, the decomposition rates of the base oils after the elapse of 65 hours were measured.

TABLE 8

|  | Comparative Example 22 | Comparative Example 23 | (wt %)<br>Comparative Example 24 |
|---|---|---|---|
| Lubricating oil composition | 27 | 28 | 29 |
| Types of base oil | MPDC9 | DOS | MPDC11 |
| base oil | 97.9 | 97.9 | 97.9 |
| IRGANOX L 06 | 2 | 2 | 2 |
| IRGAMET 39 | 0.05 | 0.05 | 0.05 |
| IRGACOR L12 | 0.05 | 0.05 | 0.05 |

TABLE 9

|  | Example 20 | Example 21 | (wt %)<br>Example 22 |
|---|---|---|---|
| Lubricating oil composition | 30 | 31 | 32 |
| Types of base oil | Compound 10 | Compound 5 | Compound 3 |
| base oil | 93.9 | 93.88 | 93.88 |
| APAN | 5.40 | 5.40 | 5.40 |
| 522A | 0.60 | 0.60 | 0.60 |
| IRGAMET 39 | 0.05 | 0.05 | 0.05 |
| IRGACOR L12 | 0.05 | 0.05 | 0.05 |

Figure 7:
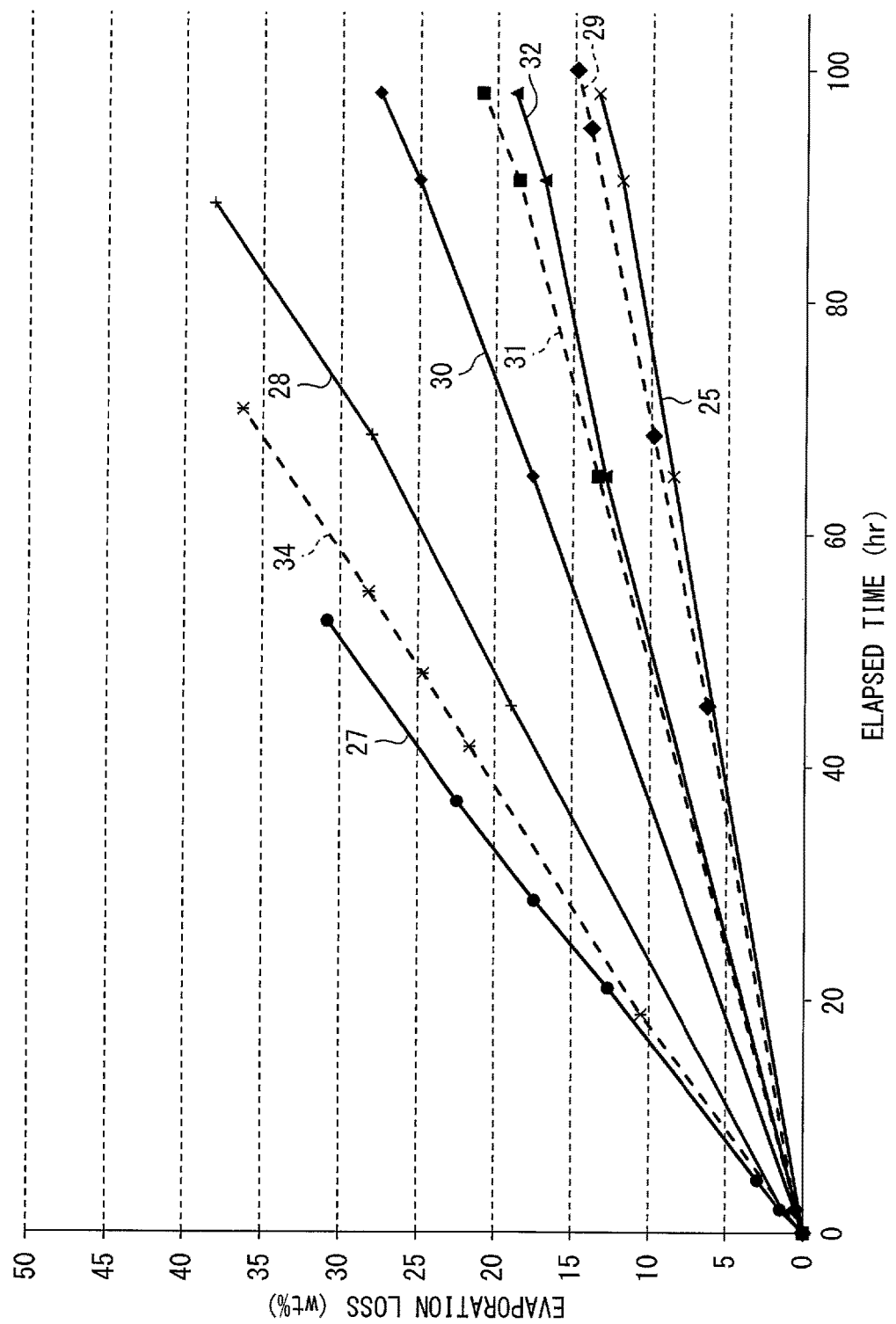
FIG. 7 is a graph showing results of measurement of evaporation losses of lubricant compositions prepared in Examples 18 and 20 to 22 of the present invention and in Comparative Examples 22 to 24.

FIG. 7 shows the result of the evaporation loss measurement together with the result obtained in Example 18. Table 10 shows the result of the measurement of the decomposition rates of the base oils after the elapse of 65 hours.

TABLE 10

|  | Lubricating oil composition | Types of base oil | Decomposition rate of base oil after elapse of 65 hours (%) |
|---|---|---|---|
| Example 18 | 25 | Compound 6 | 0 |
| Example 20 | 30 | Compound 10 | 0 |
| Example 21 | 31 | Compound 5 | 0 |
| Example 22 | 32 | Compound 3 | 0 |
| Example 24 | 34 | Compound 1 | 0 |
| Comparative Example 22 | 27 | MPDC9 | 68 |
| Comparative Example 24 | 29 | MPDC11 | 63 |

TABLE 10-continued

| Lubricating oil composition | Types of base oil | Decomposition rate of base oil after elapse of 65 hours (%) |
|---|---|---|
| Comparative Example 23 | DOS | 100 |

The existing lubricant compositions 27 and 28 contain MPDC9 and DOS, which are diesters, as base oils, respectively. As shown in FIG. 7, the existing lubricant compositions 27 and 28 showed greater evaporation losses, as compared to the lubricant compositions obtained in Examples 20 to 22, 24, and Example 18. As can be seen in Table 10, the existing lubricant compositions 27 and 28 each have the decomposition rate of the base oil after the elapse of 65 hours exceeding 60% and are poor in moisture resistance. Further, the existing lubricant composition containing MPDC11, which is diester, as a base oil, has little evaporation loss. However, as can be seen in Table 10, such an existing lubricant composition has the decomposition rate of the base oil after the elapse of 65 hours exceeding 60% and is poor in moisture resistance. In contrast, the lubricant compositions obtained in Examples 20 to 22, 24, and Example 18 are excellent in low evaporability and moisture resistance.

[Physical Property Evaluation of Aliphatic Ether Compound in Accordance with the Present Invention]

The aliphatic ether compounds obtained in the Synthesis Examples and the existing oils were evaluated on viscosity and low-temperature fluidity.

Results are shown in Tables 11 to 13.

TABLE 11

| | Compound 1 | Compound 3 | Compound 5 | Compound 6 | DOS | MPDC9 | MPDC11 |
|---|---|---|---|---|---|---|---|
| 40° C. kinetic viscosity (cSt) | 7.97 | 11.38 | 10.36 | 12.19 | 11.82 | 9.01 | 12.79 |
| 100° C. kinetic viscosity (cSt) | 2.51 | 3.29 | 3.17 | 3.57 | 3.24 | 2.79 | 3.64 |
| Viscosity index | 155 | 173 | 191 | 194 | 151 | 171 | 186 |
| Molecular weight | 431 | 487 | 459 | 487 | 427 | 399 | 455 |

TABLE 12

| | DOS | Compound 3 | Compound 5 | Compound 6 |
|---|---|---|---|---|
| 0° C. Absolute viscosity (mPa · s) | 46.3 | 45.8 | 36.4 | 45.3 |
| 25° C. Absolute viscosity (mPa · s) | 14.1 | 14.1 | 12.0 | 14.4 |

TABLE 13

| | Compound 1 | Compound 3 | Compound 5 | Compound 6 | DOS | MPDC9 | MPDC11 |
|---|---|---|---|---|---|---|---|
| Pour point (° C.) | <−40 | <−40 | −15 | −5 | <−40 | −25 | −5 |

As shown in Table 11, it can be said that the compounds 1, 3, 5, and 6 obtained in the Synthesis Examples have lower viscosities for their molecular weights, as compared to MPDC9, MPDC11, and DOS, which are the existing diesters. The compounds 1, 3, 5, and 6 were also confirmed to have viscosity indices that are higher than or equal to those of the existing diesters.

As shown in Table 12, the compounds 3, 5, and 6 obtained in the Synthesis Examples were confirmed to have lower viscosities for their molecular weights, as compared to the DOS, which is the existing diester.

As shown in Table 13, the compounds 1, 3, 5, and 6 obtained in the Synthesis Examples were confirmed to have pour points that are lower than or equal to those of MPDC9, MPDC11, and DOS, which are the existing diesters.

INDUSTRIAL APPLICABILITY

A lubricant composition in accordance with the present invention has physical properties such as low viscosity, low evaporability, low-temperature fluidity, and a high viscosity index, induces less metallic corrosion that can occur on hydrolysis, and has less adverse effect on an organic material. The lubricant composition in accordance with the present invention can therefore be suitably used not only as a bearing oil for a bearing, but also as a bearing oil for a fluid bearing, a bearing oil for an impregnated bearing, a raw material for a grease, a raw material for a freezer oil, and the like. As such, the present invention is remarkably high in industrial use value in all technical fields where lubricant compositions are used.

The invention claimed is:

1. A lubricant composition comprising:
an aliphatic ether compound that serves as a base oil; and
an antioxidant including at least alkylated phenylnaphthylamine and phosphite ester,
wherein a sum of individual amounts of the alkylated phenylnaphthylamine and the phosphite ester, which are contained in the lubricant composition, is 3% to 8% by weight relative to a total amount of the base oil, and
the alkylated phenylnaphthylamine and the phosphite ester are used in such a ratio that the alkylated phenylnaphthylamine and the phosphite ester account for 85% to 95% by weight and 5% to 15% by weight, respectively, of the sum of the individual amounts of the alkylated phenylnaphthylamine and the phosphite ester.

2. The lubricant composition according to claim 1, wherein the aliphatic ether compound is an aliphatic ether compound having 8 to 300 carbon atoms in one molecule and having 1 to 150 oxygen atoms in one molecule.

3. The lubricant composition according to claim 1, wherein the aliphatic ether compound is 2-(2-ethylhexyloxy)ethyl ether compound.

4. The lubricant composition according to claim 1, wherein the aliphatic ether compound is at least one compound selected from the group consisting of compounds having respective structures represented by the following chemical formulae (1) to (10):

[Chem. 1]

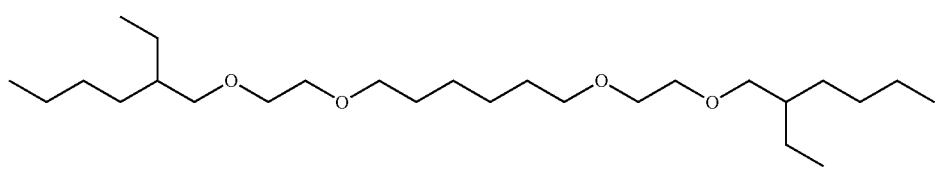
(1)

[Chem. 2]

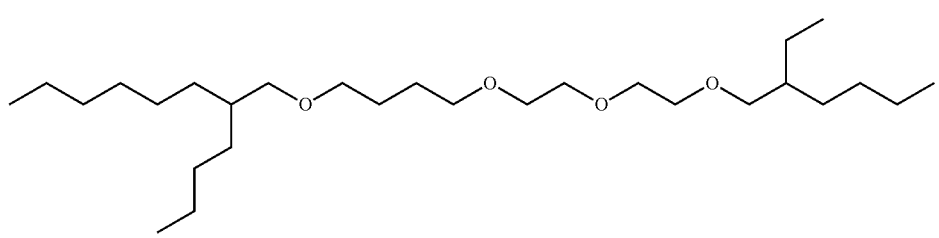
(2)

[Chem. 3]

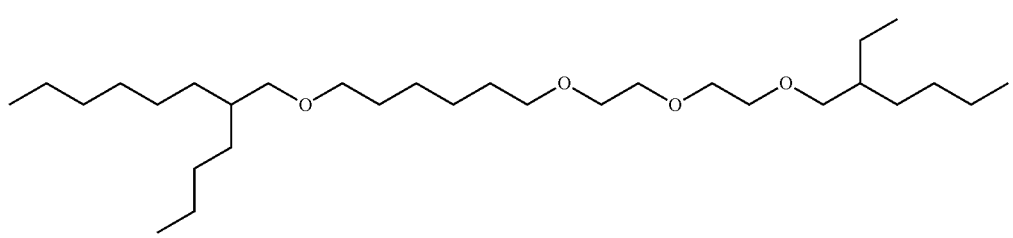
(3)

[Chem. 4]

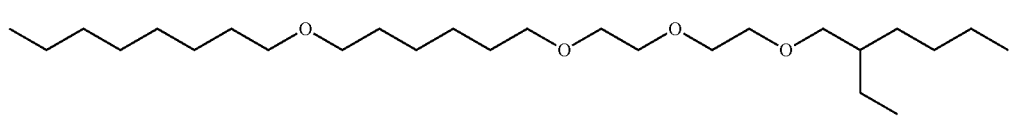
(4)

[Chem. 5]

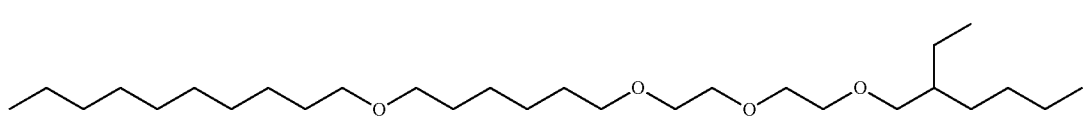
(5)

[Chem. 6]

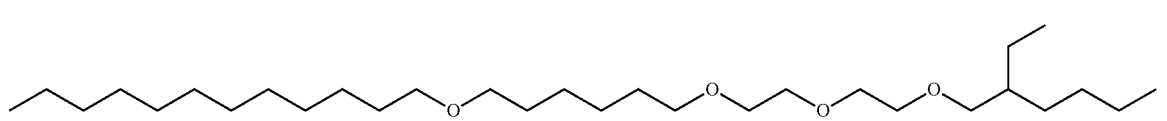
(6)

[Chem. 7]

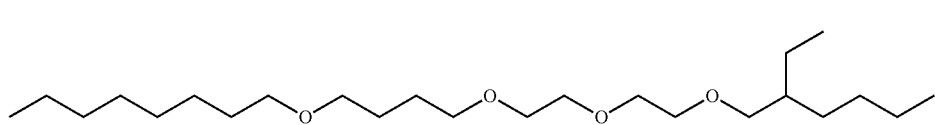
(7)

[Chem. 8]

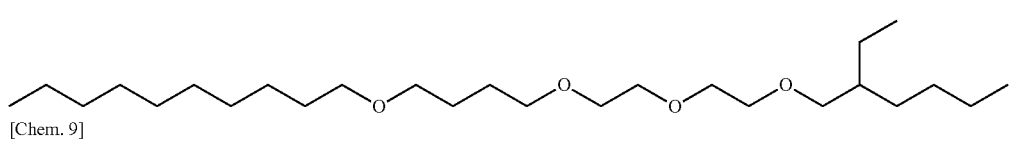
(8)

[Chem. 9]

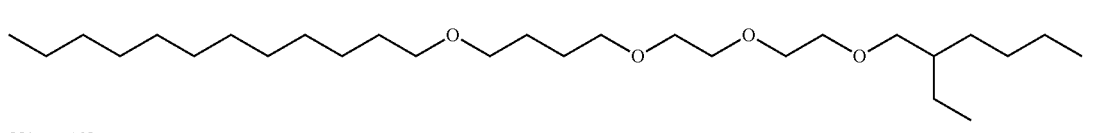
(9)

[Chem. 10]

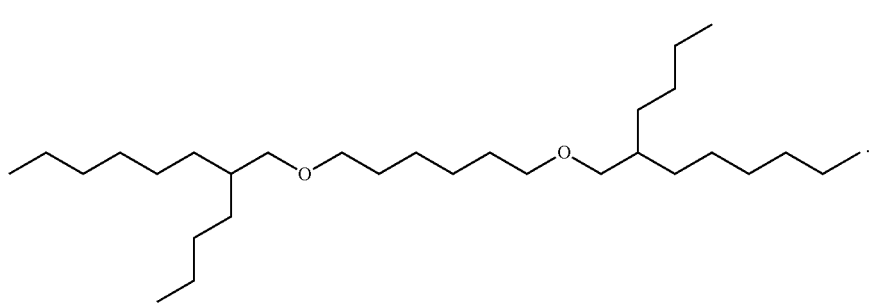
(10)

5. The lubricant composition according to claim 1, wherein the alkylated phenylnaphthylamine is N-phenyl-dodecylnaphthalene-1-amine or N-phenyl-octylnaphthalene-1-amine.

6. The lubricant composition according to claim 1, wherein the phosphite ester is 1,1,3-tris(2-methyl-4-ditridecylphosphite-5-t-butylphenyl)butane.

7. A bearing oil comprising a lubricant composition recited in claim 1.

8. A bearing which is lubricated with use of a lubricant composition recited in claim 1.

9. The bearing according to claim 8, which is a fluid bearing or an impregnated bearing.

10. A motor comprising a bearing recited in claim 8.

11. A method for lubricating a bearing, comprising:
lubricating a bearing with use of a lubricant composition recited in claim 1.

12. A method for producing a grease, the method comprising adding a thickener to the lubricant composition of claim 1.

13. A grease containing a lubricant composition recited in claim 1.

14. A freezer oil containing a lubricant composition recited in claim 1.

15. An aliphatic ether compound having a structure represented by any one of the following chemical formulae (1) to (9):

[Chem. 11]

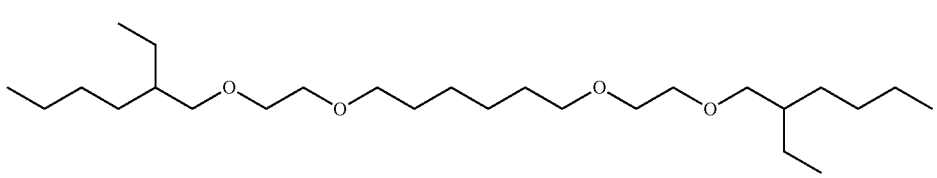
(1)

[Chem. 12]

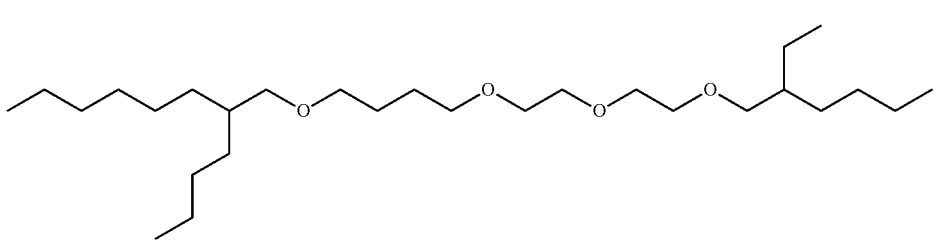
(2)

-continued
[Chem. 13]
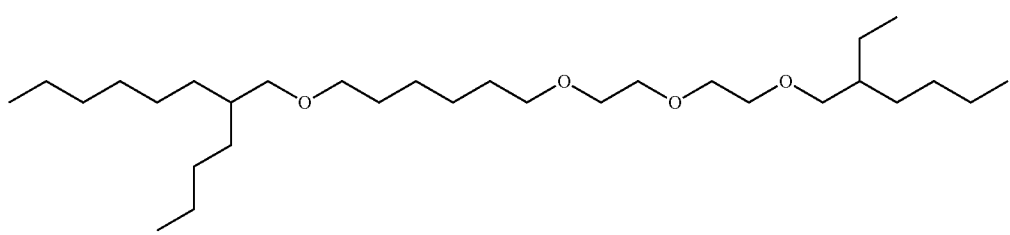
(3)
[Chem. 14]
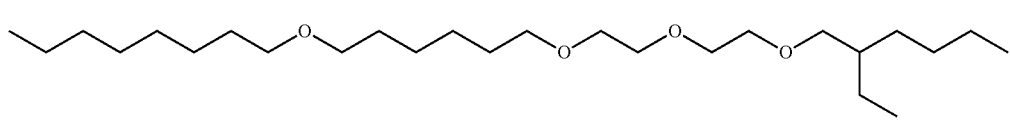
(4)
[Chem. 15]
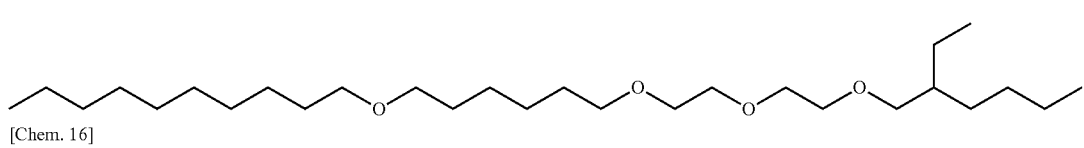
(5)
[Chem. 16]
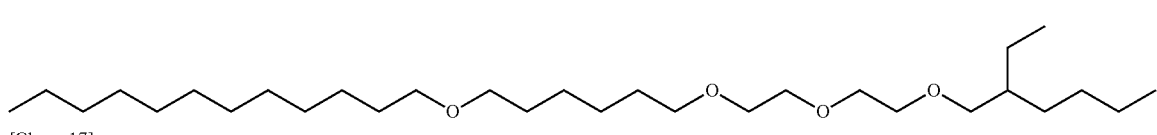
(6)
[Chem. 17]
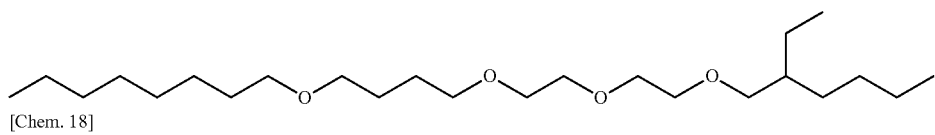
(7)
[Chem. 18]
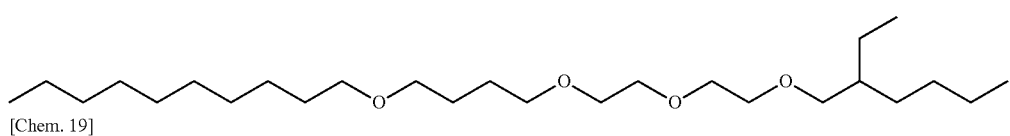
(8)
[Chem. 19]
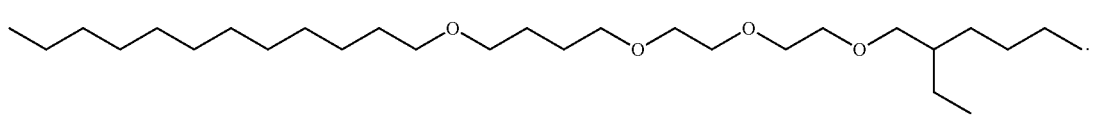
(9)
* * * * *